US011021512B2

(12) United States Patent
Henkel et al.

(10) Patent No.: US 11,021,512 B2
(45) Date of Patent: Jun. 1, 2021

(54) METHOD OF PREPARING PEPTIDES COMPRISING A LIPOPHILICALLY MODIFIED LYSINE SIDE CHAIN

(71) Applicant: SANOFI, Paris (FR)

(72) Inventors: Bernd Henkel, Frankfurt am Main (DE); Norbert Pleuss, Frankfurt am Main (DE); Rolf-Ludwig Hoerlein, Frankfurt am Main (DE)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 16/338,213

(22) PCT Filed: Oct. 10, 2017

(86) PCT No.: PCT/EP2017/075773
§ 371 (c)(1),
(2) Date: Mar. 29, 2019

(87) PCT Pub. No.: WO2018/069295
PCT Pub. Date: Apr. 19, 2018

(65) Prior Publication Data
US 2020/0024304 A1 Jan. 23, 2020

(30) Foreign Application Priority Data
Oct. 10, 2016 (EP) ..................... 16306332

(51) Int. Cl.
C07K 1/30 (2006.01)
C07K 1/00 (2006.01)
C07K 1/107 (2006.01)
C07K 1/34 (2006.01)
C07K 14/575 (2006.01)

(52) U.S. Cl.
CPC ............ C07K 1/006 (2013.01); C07K 1/1077 (2013.01); C07K 1/30 (2013.01); C07K 1/34 (2013.01); C07K 14/57563 (2013.01)

(58) Field of Classification Search
CPC ........ C07K 1/006; C07K 1/1077; C07K 1/30; C07K 1/34; C07K 14/57563; C07K 14/46; C07K 14/605; B01J 2219/00725
See application file for complete search history.

(56) References Cited

U.S. PATENT DOCUMENTS

| 2012/0196798 | A1* | 8/2012 | Wang | .................. | C07K 14/605 514/5.3 |
| 2012/0283170 | A1* | 11/2012 | Lau | .......................... | A61P 9/12 514/1.9 |

FOREIGN PATENT DOCUMENTS

| EA | 023925 B1 | 7/2016 |
| EP | 2 460 825 A1 | 6/2012 |
| WO | WO 2010/043566 A2 | 4/2010 |
| WO | WO 2011/058053 A1 | 5/2011 |
| WO | WO 2011/058082 A1 | 5/2011 |
| WO | WO 2011/104378 A1 | 9/2011 |
| WO | WO 2011/134471 A1 | 11/2011 |
| WO | WO 2013/167454 A1 | 11/2013 |
| WO | WO 2013/186240 A2 | 12/2013 |
| WO | WO 2014/056872 A1 | 4/2014 |
| WO | WO 2014/096145 A1 | 6/2014 |
| WO | WO 2014/096148 A1 | 6/2014 |
| WO | WO 2014/096149 A1 | 6/2014 |
| WO | WO 2014/096150 A1 | 6/2014 |
| WO | WO 2015/155139 A1 | 10/2015 |
| WO | WO 2015/155140 A1 | 10/2015 |
| WO | WO 2015/155141 A1 | 10/2015 |
| WO | WO 2008/023050 A1 | 2/2018 |

OTHER PUBLICATIONS

Technical Bulletin, Applied Biosystems, May 1998, 1-12 (Year: 1998).*
International Search Report and Written Opinion dated Jan. 10, 2018 in related PCT Application No. PCT/EP2017/075773 filed Oct. 10, 2017 (14 pages).
Buse at al., Liraglutide once a day versus exenatide twice a day for type 2 diabetes: a 26-week randomised, parallel-group, multinational, open-label trial (LEAD-6), Lancet, 2009, vol. 374, pp. 39-47.
Chhabra et al., "An appraisal of new variants of Dde amine protecting group for solid phase peptide synthesis", Tetrahedron Letters, 1998, vol. 39, pp. 1603-1606.
Drucker et al., "Liraglutide", Nature Reviews Drug Discovery, 2010, vol. 9, pp. 267-268.
Eng et al., "Isolation and characterization of exendin-4, an exendin-2 analogue, from Heloderma suspectum venom", The Journal of Biological Chemistry, 1992, vol. 267, No. 11, pp. 7402-7405.
Extended European Search Report for European Patent Application No. 16306332.4, dated Mar. 14, 2017.
Jones, The Chemical Synthesis of Peptides, Clarendon Press, Oxford, 1991 (abstract).
King et al., "A cleavage method which minimizes side reactions following Fmoc solid phase peptide synthesis", Int. J. Peptide Protein Res., 1990, vol. 36, pp. 255-266.
Ogawa et al., "Studies on Peptides. LXXIX. By-Products derived from Nα-Protected Tryptophan by Acids", Faculty of Pharmaceutical Sciences, Kyoto University, 1978, vol. 26, pp. 3144-3149.
Pennington and Dunn, Methods in Molecular Biology, vol. 35, Peptid Synthesis Protocols, Humana Press, Totowa, New Jersey, 1994 (abstract).

* cited by examiner

Primary Examiner — Sudhakar Katakam
(74) Attorney, Agent, or Firm — Lathrop GPM LLP; James H. Velema, Esq.

(57) ABSTRACT

The present invention relates to a method of preparing a lysine side-chain modified peptide by solid phase peptide synthesis.

24 Claims, No Drawings
Specification includes a Sequence Listing.

METHOD OF PREPARING PEPTIDES COMPRISING A LIPOPHILICALLY MODIFIED LYSINE SIDE CHAIN

CROSS-REFERENCE TO RELATED APPLICATIONS

This application is a 35 U.S.C. § 371 filing of International Patent Application No. PCT/EP2017/075773, filed Oct. 10, 2017, which claims priority to European Patent Application No. 16306332.4, filed Oct. 10, 2016, the entire contents of which are incorporated herein by reference.

FIELD OF THE INVENTION

The present invention relates to a method of preparing a lysine side-chain modified peptide by solid phase peptide synthesis.

BACKGROUND OF THE INVENTION

Compounds of interest are exendin-4 derivatives comprising a lipophilically modified lysine side chain. Exendin-4 (SEQ ID NO. 3) is a 39 amino acid peptide which is produced by the salivary glands of the Gila monster (*Heloderma suspectum*) (Eng, J. et al., J. Biol. Chem., 267:7402-05, 1992). Exendin-4 is an activator of the glucagon-like peptide-1 (GLP-1) receptor, whereas it does not activate significantly the glucagon receptor. A modification with fatty acid acylated residues, particularly in position 14, as described e.g. in WO2013/186240, WO2014/056872, WO2014/096145, WO2014/096148, WO2014/096149, WO2014/096150, WO2015/155139, WO2015/155140, and WO2015/155141, results in exendin-4 derivatives with high activity not only at the GLP-1 receptor but also at the glucagon receptor when compared to the corresponding non-acylated exendin-4 derivatives.

Liraglutide (SEQ ID NO.: 4) is a marketed chemically modified GLP-1 analog in which, among other modifications, a fatty acid is linked to a lysine in position 20 leading to a prolonged duration of action (Drucker D J et al., Nature Drug Disc. Rev. 9, 267-268, 2010; Buse, J. B. et al., Lancet, 374:39-47, 2009).

EP 2 460 825 A1 discloses GLP-1 analogues bearing a C-terminal lysine residue, which is modified by a lipohilic substituent of formula $R_1$—$(CH_2)_n$—CO—, with $R_1$ being methyl or carboxyl and n being an integer from 8-25. In contrast to the present invention, the peptides of EP 2 460 825 A1 are synthesized starting from the C-terminal lysine, which is lipophilically modified in a first step; subsequent to addition of the lipophilic substituent, the remaining amino acids of the desired peptide are added via SPPS. Further, the Mtt (4-methyltrityl) lysine protecting group is removed by one incubation with 1% trifluoroacetic acid (TFA)/dichloromethane (DCM) after swelling the dried residue with 500 ml dimethyl formamide (DMF) for 30 min (see Examples). It has to be noted that remaining DMF has a neutralizing effect on 1% TFA in DCM, thus making the cleavage of the Mtt group incomplete.

WO 2008/023050 A1 relates to a variety of acylated Exendin-4 compounds. In the Example section of this document, synthesis of the claimed compounds is described. According to WO 2008/023050 A1, monomethoxytrityl (Mmt)- or Mtt-protection is removed using a solution of 2% TFA and 2-3% triisopropylsilane (TIS) in DCM, which is more complex than the TFA in DCM solution used according to the present invention. Further, WO 2008/023050 A1 is silent with regard to a predrying of the resin after assembly of the amino acid sequence is complete.

Similarly, WO 2011/104378 A1, which relates to peptidic melanocortin receptor modulators and WO 2013/167454 A1, which relates to double-acylated GLP-1 derivatives acylated at lysine at position 26 (K26) and 37 (K37) with respect to wild-type GLP-1(7-37), are silent as to a predrying step of the resin after assembly of the amino acid sequence, and fail to disclose or even suggest a cleavage solution for removal of Mmt-/Mtt-protecting groups as presently claimed. In both applications, the cleavage solution is more complex.

WO 2015/155141 A1, which is incorporated by reference herein, relates to peptidic dual GLP-1/glucagon receptor agonists derived from exendin-4, which contain an acylated lysine. Again, this document does not disclose or suggest predrying of the resin or a neutralization of the resin-bound peptide before coupling of the linker moiety between peptide and lipophilic moiety.

A preferred way of manufacturing peptides that may contain unnatural amino acids and side-chain modifications, e.g. of the ε-amino-groups of lysine or of the δ-amino group of ornithine or of the γ-amino group of 2,4-diaminobutyric acid or of the β-amino group of 2,3-diaminopropionic acid is solid phase synthesis on a suitable resin. Solid phase peptide synthesis (SPPS) is a proven method for the synthetic access to peptides (examples are given in: Stewart and Young, Solid Phase Peptide Synthesis, Pierce Chemical Co., Rockford, Ill., 1984).

Solid-phase synthesis of a peptide is generally started with an N-terminally protected amino acid derivative to a solid support-bearing linker. A solid support can be any polymer which is compatible to the solvents used in SPPS and allows coupling of an amino acid derivative with its carboxy group onto the resin (e.g. a trityl resin, a chlorotrityl resin, a Wang-resin when a peptide acid is desired, or a Rink-resin, a Sieber-resin when a peptide amide has to be obtained by using the Fmoc-strategy). Stability of the polymer support must be given under the conditions used for deprotection of the α-amino group during peptide synthesis.

After the first N-terminally protected amino acid has been coupled onto the linker-resin construct, the N-terminal protecting group is cleaved with bases, such as with piperidine/ dimethylformamide mixtures (Fmoc-strategy). The liberated amino group is reacted with a Fmoc-protected amino acid derivative using coupling reagents such as e.g. BOP (Benzotriazole-1-yl-oxy-tris(dimethylamino)-phosphonium hexafluorophosphate), HBTU (2-(1H-Benzotriazole-1-yl)-1, 1,3,3-tetramethylaminium hexafluorophosphate), HATU (O-(7-Azabenzotriazol-1-yl)-N,N,N',N'-tetramethyluronium hexafluorophosphate) together with a tertiary base like DIPEA (Diisopropyl ethylamine) or NMM (N-Methylmorpholine) or alternatively with DIC (N,N'-diisopropyl carbodiimide)/HOBt Hydrate (1-hydroxybenzotriazol). This process is repeated until the desired amino acid sequence is obtained.

Reactive side-chain functions of the amino acid derivatives are usually blocked with suitable protecting groups that are stable under the conditions used for solid phase peptide synthesis. They are removed concomitantly with the cleavage of the desired product from the resin under the same conditions after the peptide has been assembled on the solid phase. Protecting groups and the procedures for their introduction can be found in Greene and Wuts, Protective Groups in Organic Synthesis, 3$^{rd}$ ed., Wiley & Sons, New York, 1999 or in Kocienski, Protecting Groups, Georg Thieme Verlag, Stuttgart, New York, 1994.

There is also a possibility to remove side-chain protecting groups selectively in SPPS in order to modify them. The conditions for the removal of such a protecting group must be such that all other protecting groups remain intact. A lysine may be protected with the 1-(4,4-dimethyl-2,6-dioxo-cyclohexylidene)-3-methyl-butyl (ivDde) or the 1-(4,4-dimethyl-2,6-dioxocyclohexylidene)-ethyl (Dde) group (see Chhabra et al., Tetrahedron Lett. 39, 1603, 1998) which is labile to a hydrazine-solution in DMF. Once the N-terminal protecting group as well as all the side-chain protecting groups are with acid labile protecting groups, the ivDde- or the Dde-protecting group can be cleaved with hydrazine in DMF. The liberated amino group from the lysine side-chain can be modified thereafter e.g. with other Fmoc-amino acids or fatty acids. The same procedure can be applied to ornithine, 2,4-diamino butyric acid or 2,3-diamino propionic acid.

The peptide can finally be cleaved from the resin concomitantly with all the side chain protecting groups with the use of trifluoroacetic acid containing cocktails e.g. King's cocktail (King et al., Int. J. Peptide Protein Res. 36, 255-266, 1990), comprising trifluoroacetic acid (TFA), phenol, water, thioanisole and 1,2-ethanedithiol (EDT). After a certain reaction time the resin is filtered off and the crude peptide precipitated in ether e.g. diethyl ether, methyl tert-butyl ether or diisopropyl ether. The precipitate can be filtered off or separated from the solution by centrifugation.

If necessary, the crude peptide can be purified by preparative chromatography on a C18-column. For purification several runs might be needed to give a purity of >90% or even more. The final run will usually be the salification run where the desired counter-ion e.g. acetate will be determined. The fractions are analyzed by HPLC and pooled according to defined criteria. The solvent can be removed e.g. by distillation, lyophilisation, spray drying or combinations thereof. In the end the purified peptide is obtained.

BRIEF SUMMARY OF THE INVENTION

Provided herein is a novel method for solid phase synthesis of lysine side-chain modified peptides. These peptides are in particular exendin-4 derivatives, in which at least one amino acid, particularly methionine at position 14, is replaced by lysine, which is further substituted with a nonpolar, lipophilic residue (e.g. a fatty acid optionally combined with a linker).

It was surprisingly found that by following a specific sequence of steps, the amount of undesired side-products can be greatly decreased, resulting in an increased yield of desired product at higher purity.

Accordingly, the present invention is directed to a method of preparing an isolated peptide comprising a lipophilically modified lysine side chain, comprising the steps of:
(i) assembling the amino acid sequence of said peptide with protected reactive functional groups in the side chains in a step-wise manner using solid phase peptide synthesis (SPPS), wherein the side chain of lysine to be modified is protected by a trityl-based protecting group, particularly monomethoxytrityl (Mmt) or 4-methyltrityl (Mtt);
(ii) drying the solid phase resin after the assembling of the amino acid sequence has been completed;
(iii) treating the dried resin several times with a solution of trifluoroacetic acid (TFA) in dichloromethane (DCM) in order to deprotect the lysine side chain to be modified;
(iv) neutralizing the resin;
(v) coupling at least one activated 9-fluorenylmethyloxycarbonyl (Fmoc)-bound linker moiety to the deprotected lysine side chain;
(vi) deprotecting the terminal functional group of the linker coupled to the lysine side chain in step (v);
(vii) coupling an activated lipophilic moiety, particularly an activated fatty acid, to the deprotected terminal functional group of the linker of step (vi);
(viii) drying the resin; and
(ix) cleaving the peptide from the resin.

In certain embodiments, the isolated peptide is an exendin-4 derivative having a length of between 30 and 44, particularly between 38 and 40 amino acids, wherein preferably (i) the sequence identity to wild-type exendin-4 in the region corresponding to amino acids 1-13 of wild-type exendin is at least 65%, and/or (ii) the sequence identity to wild-type exendin-4 in the region corresponding to amino acids 22-39 of wild-type exendin is at least 70%, and/or (iii) the lipophilically modified lysine side chain is at position 14 (Lys(14)) with respect to the amino acid positions of wild-type exendin-4. In certain preferred embodiments, the isolated exendin-4 derivative has the amino acid sequence H-dS-Q-G-T-F-T-S-D-L-S-K-Q-K(γE-Palm)-E-S-K-A-A-Q-D-F-I-E-W-L-K-A-G-G-P-S-S-G-A-P-P-P-S-NH$_2$ (SEQ ID NO.: 1).

In some embodiments, the number of TFA in DCM treatments in step (iii) is adjusted such that the yield of modified lysine side chain in step (ix) is at least 85%, particularly at least 90%, more particularly at least 95%. The yield is given in percent as compared to peptide without modified lysine side chain (i.e. a yield of 85% means that 85% of the peptide has the modified lysine side chain and 15% of the peptide remains with an unmodified lysine side chain.

For example, in step (iii), the dried resin may be treated at least seven times for at least 5 minutes, particularly nine times for at least 10 minutes or nine times for at least 15 min, with a solution of about 1% (v/v) TFA in DCM. It is possible to use TFA up to about 1.5% (v/v). However, concentrations of 2% (v/v) TFA and higher are disadvantageous, because the selectivity of the cleavage is then reduced; in particular, solutions containing ≥2% (v/v) TFA not only cleave the, e.g., monomethoxytrityl protecting group at the lysine side chain of interest, but also, e.g., Boc protecting groups at other amino acid residues. This can cause undesired multiple acylations in subsequent steps of the procedure.

In particular embodiments, the method of the invention further comprises the steps of:
(viii-a) analyzing the deprotection yield of step (iii) by cleaving a test sample of the resin bound peptide; and
(viii-b) optionally repeating steps (iii) to (viii-a) until the content of cleaved peptide containing the modified lysine side chain is at least 85%, particularly at least 90%, more particularly at least 95% compared to peptide without modified lysine side chain.

In certain embodiments, analyzing the deprotection yield may comprise
(viii-a1) removing a test sample of the resin from the total reaction batch and cleaving the peptide from the test sample under the same conditions and with the same cleavage cocktail as in step (ix); and
(viii-a2) determining the content of cleaved peptide containing the modified lysine side chain in comparison to the peptide without modified lysine side chain, in particular by high pressure liquid chromatography (HPLC) or a combination of HPLC and mass spectrometry (LC-MS).

In certain embodiments, the cleavage of step (ix) is performed with a cleavage cocktail comprising at least 90% (v/v) trifluoroacetic acid and at least 1% (v/v) ethanedithiol, which is free of thioanisole and ethylmethylsulfide.

In certain embodiments, the cleavage cocktail further comprises a suitable indole compound, particularly 3-methylindole.

In some embodiments, the cleavage cocktail particularly consists of 91-93% (v/v) trifluoroacetic acid, 1-6% (v/v) phenol and 1-8% (v/v) ethanedithiol. In other embodiments, the cleavage cocktail consists of 96-98% (v/v) trifluoroacetic acid and 2-4% (v/v) ethanedithiol.

In yet further embodiments, the cleavage of step (ix) is performed with a cleavage cocktail comprising at least 80% (w/w) trifluoroacetic acid and at least 1% (w/w) 1,2-ethanedithiol, which is free of thioanisole and ethylmethylsulfide.

In certain embodiments, the cleavage cocktail consists of 88.2-98.3% (w/w) trifluoroacetic acid, 1-4.3% (w/w) 1,2-ethanedithiol and 0.7-7.5% (w/w) 3-methylindole.

The cleavage of step (ix) may e.g. be performed at 5-15° C., 15-22° C. and/or 22-30° C., particularly at 25° C. The volume of the cleavage cocktail per gram of peptide on resin may for example be from 9.5 ml to 5.5 ml, particularly from 7.0 ml to 6.0 ml. The cleavage of step (ix) may e.g. be performed for 2-3 hours, in particular 2-3 hours or 2.0-2.5 hours at 25° C. or 1-1.5 hours at 30° C., with stirring.

Drying of the resin in step (ii) may, in certain embodiments, be performed under inert gas, e.g. nitrogen at room temperature, subsequent to washing the peptide on resin at least once with an aliphatic alcohol and at least once with a dialkyl ether.

The neutralization in step (iv) may for example be performed by at least one incubation with a 1%-5% solution of a tertiary alkylamine in an organic polar aprotic solvent, e.g. diisopropyl ethylamine (DIPEA) in dichloromethane or N-methylmorpholine (NMM) in dichloromethane or triethylamine in dichloromethane, for at least 10 minutes, optionally followed by determination of the pH of the solvent mixture after the neutralization step, and washing the peptide on resin at least once with said solvent and at least once with a further polar aprotic solvent, e.g. dimethylformamide (DMF).

Deprotection in step (vi) may, in certain embodiments, be performed by treating peptide on resin at least once for at least 5 minutes with a base, followed by at least one washing step.

Drying of the resin in step (viii) may, in certain embodiments, be performed under vacuum, subsequent to washing the peptide on resin, in particular under vacuum of ≤70 mbar.

According to some embodiments, the claimed method further comprises the steps of:
(x) filtering the peptide solution after cleavage;
(xi) distilling the filtered peptide solution under vacuum;
(xii) adding the residual fraction from the distillation to an antisolvent comprising a dialkyl ether and a heptane;
(xiii) stirring the precipitated solution
(xiv) filtering the precipitated solution;
(xv) washing the precipitate; and
(xvi) drying the wet peptide.

Subsequent to step (x), the resin filter cake may in some embodiments be rinsed at least once, e.g. 3 times, with a suitable rinsing solution, e.g. TFA.

In step (xi), the distillation may for example be performed at a vacuum of ≤50 mbar at a temperature of ≤30° C.

Further, the antisolvent used in step (xii) may be, in some embodiments, a mixture consisting of diisopropyl ether (DIPE) and n-heptane, particularly a mixture of DIPE and n-heptane in a ratio of from 25:75 (v/v) to 35:65 (v/v).

In step (xiii), the precipitated solution may, for example, be stirred for 1-20 hours at 10-15° C.

In step (xv), the precipitate on the filter may, subsequent to rinsing with a suitable organic solvent, e.g. ethyl acetate, be washed at least once by resuspending the precipitate in a suitable organic solvent, e.g. ethyl acetate, stirring the resulting suspension, e.g. for 30-60 minutes, and filtering off the organic solvent. This procedure may be repeated 1-5 times, particularly 2-4 times, more particularly 3-5 times with ethyl acetate according to some embodiments.

In some embodiments, the wet peptide is dried under vacuum in step (xvi), e.g. at 20-25° C., in particular under vacuum of ≤70 mbar at 20-25° C. and nitrogen stripping.

In some embodiments, the claimed method comprises the steps of:
(i) assembling the amino acid sequence of a peptide of SEQ ID NO.: 1 with protected reactive functional groups in the side chains in a step-wise manner using solid phase peptide synthesis (SPPS), wherein the side chain of lysine 14 is protected by monomethoxytrityl (Mmt);
(ii) drying the solid phase resin for at least 5 hours at room temperature after the assembling of the amino acid sequence has been completed;
(iii) treating the dried resin nine times for 10 minutes each with a solution of 1% (v/v) trifluoroacetic acid (TFA) in dichloromethane (DCM) in order to deprotect the lysine side chain at position 14;
(iv) neutralizing the resin with a solution of 3% diisopropyl ethylamine (DIPEA) in DCM, until the pH of the solution remains at ≥8;
(v) coupling an activated Fmoc-Glu-OtBu linker moiety to the deprotected lysine side chain under basic conditions;
(vi) cleaving the Fmoc group of the linker coupled to the lysine side chain in step (v) with 20% piperidine in DMF;
(vii) coupling activated palmitic acid to the deprotected terminal functional group of the linker of step (vi);
(viii) drying the resin;
(viii-a) analyzing the deprotection yield of step (iii) by cleaving a test sample of the resin bound peptide;
(viii-b) repeating steps (iii) to (viii-a) until the content of cleaved peptide containing the modified lysine side chain is at least 85%;
(ix) and cleaving the peptide from the resin at 25° C. using a cleavage cocktail comprising at least 90% (v/v) trifluoroacetic acid and at least 1% (v/v) ethanedithiol, which is free of thioanisole and ethylmethylsulfide.

In some embodiments, the claimed method comprises the steps of:
(i) assembling the amino acid sequence of a peptide of SEQ ID NO.: 1 with protected reactive functional groups in the side chains in a step-wise manner using solid phase peptide synthesis (SPPS), wherein the side chain of lysine 14 is protected by monomethoxytrityl (Mmt);
(ii) drying the solid phase resin for at least 5 hours at room temperature after the assembling of the amino acid sequence has been completed;
(iii) treating the dried resin nine times for 10 minutes each with a solution of 1% (v/v) trifluoroacetic acid (TFA) in dichloromethane (DCM) in order to deprotect the lysine side chain at position 14;

(iv) neutralizing the resin with a solution of 3% diisopropyl ethylamine (DIPEA) in DCM, until the pH of the solution remains at ≥8;
(v) coupling an activated Fmoc-Glu-OtBu linker moiety to the deprotected lysine side chain under basic conditions;
(vi) cleaving the Fmoc group of the linker coupled to the lysine side chain in step (v) with 20% piperidine in DMF;
(vii) coupling activated palmitic acid to the deprotected terminal functional group of the linker of step (vi);
(viii) drying the resin;
(viii-a) analyzing the deprotection yield of step (iii) by cleaving a test sample of the resin bound peptide;
(viii-b) repeating steps (iii) to (viii-a) until the content of cleaved peptide containing the modified lysine side chain is at least 85%;
(ix) cleaving the peptide from the resin using a cleavage cocktail consisting of 96.0-97.5% (w/w) TFA, 1.7-2.6% (w/w) EDT and 0.7-1.5% (w/w) 3-methylindole;
(x) filtering the peptide solution after cleavage at room temperature;
(xi) distilling the filtered peptide solution under vacuum at ≤30° C.;
(xii) adding the residual fraction from the distillation to an antisolvent consisting of DIPE and n-heptane in a ration of from 25:75 (v/v) to 35:65 (v/v);
(xiii) stirring the precipitated solution at 10-15° C. for 1-18 hours;
(xiv) filtering the precipitated solution;
(xv) washing the precipitate 4-5 times by (xv-a) resuspending the precipitate in ethyl acetate, (xv-b) stirring the resulting suspension for 30-60 minutes and (xv-c) filtering off ethyl acetate; and
(xvi) drying the wet peptide under vacuum.

DETAILED DESCRIPTION OF THE INVENTION

The above-described inventive method of preparing an isolated peptide comprising a lipophilically modified lysine side chain comprises at least nine steps.

The first step (step (i)) concerns the synthesis of the peptide of interest via solid phase peptide synthesis (SPPS). As mentioned supra, SPPS comprises assembling the amino acid sequence of the peptide with protected reactive functional groups in the side chains in a step-wise manner. The peptide contains at least one lysine, the side chain of which is to be modified. The side chain of this at least one (e.g. one, two or three) lysine residue is protected by a trityl-based protecting group. In particular embodiments, the peptide contains only one modified lysine side chain. Trityl-based protecting groups of particular use within the present application are monomethoxytrityl (Mmt) and 4-methyltrityl (Mtt). In certain preferred embodiments, only Mmt is used as the trityl-based protecting group for the lysine residue(s) to be modified.

For SPPS according to the invention, it is possible to use, in particular, different Rink-Amide resins, for example 4-(2',4'-Dimethoxyphenyl-Fmoc-aminomethyl)-phenoxyacetamido-norleucylaminomethyl resin or 4-[(2,4-Dimethoxyphenyl)(Fmoc-amino)methyl]phenoxy acetamido methyl resin. Loadings may range between 0.1 and 1 mmol/g, particularly between 0.2 and 0.9 mmol/g. In certain embodiments, the loadings range between 0.25 and 0.6 mmol/g. In other embodiments, the loadings range between 0.2 and 0.4 mmol/g. Although it is generally possible to use any synthesis strategy SPPS, in the context of the present invention the 9-fluorenylmethyloxycarbonyl (Fmoc) strategy, which enables using milder deprotection conditions, is preferred. A suitable base, for example piperidine, particularly in a concentration of 20-50%, in dimethylformamide (DMF), is used for deprotection (i.e. removing the Fmoc group from the protected amino group of the Rink amide or, in later stages, from the α-amino group of the respective amino acid). Coupling of each amino acid to the resin or previous amino acid, respectively, is performed according to standard conditions, using e.g. 1-hydroxybenzotriazol (HOBt) hydrate and N,N'-diisopropyl carbodiimide (DIC) in DMF as coupling reagents. Coupling times for each amino acid may vary and are generally in the range of 2 to 22 hours.

The Fmoc-lysine derivative that is used for SPPS and whose side chain shall be modified, is particularly Fmoc-Lys(Mmt)-OH or Fmoc-Lys(Mtt)-OH.

The α-amino group of the N-terminal amino acid is preferably protected by a tert-butyloxycarbonyl (Boc) group. Subsequent to the addition of the N-terminal amino acid of the desired peptide, the peptide on resin is washed. At least one and up to 10 washing steps are carried out before proceeding further, in particular 4, 5, 6, 7, or 8 washing steps, more particularly 6 washing steps. Suitable washing fluids comprise an aliphatic alcohol, e.g. methanol, ethanol, n-propanol or isopropanol (IPA), and/or a dialkyl ether, e.g. diethyl ether, tert.butylmethyl ether, diisopropyl ether (DIPE) or diisobutyl ether. In certain embodiments, washing is performed with IPA and DIPE. Particularly, the peptide on resin is first washed at least once with IPA and subsequently washed at least once with DIPE. In certain preferred embodiments, the peptide on resin is first washed three times with IPA and subsequently washed three times with DIPE.

After washing, the solid phase resin with the peptide is dried (step (ii)). Drying may be performed under inert gas atmosphere, e.g. nitrogen, particularly under a continuous nitrogen stream (nitrogen stripping). Suitably, the drying step (ii) is performed for at least one hour, particularly at least 5 hours, at least 10 hours, at least 16 hours and up to 20 hours (e.g. overnight). In some embodiments, it is also possible to perform the drying step for more than 20 hours. Particularly, drying is performed at room temperature (18-24° C.). According to the prior art, the peptide on resin should not be dried before the Mmt- or Mtt-group is to be cleaved from the resin. It is generally believed that the resin shall be well swollen throughout the whole synthesis to ensure good accessibility of the peptide's N-terminus, in this case the ε-amino group of lysine. During drying according to step (ii) of the method of the present invention, the resin shrinks considerably, and it could not have been foreseen that all potential reactive sites were still freely accessible for further steps. Moreover, the skilled person would have been afraid of further disadvantages, as an additional drying step increases the duration of the synthesis, and a higher amount of solvent is required, increasing the cost of the procedure. Surprisingly, however, it was found that this intermediate drying step was advantageous and outweighs the expected disadvantages by far. For example, the predrying step is beneficial to a more complete removal of the trityl-based lysine protecting group.

The dried and shrunken resin may then be directly treated several times with a solution of trifluoroacetic acid (TFA) in dichloromethane (DCM) in order to deprotect the lysine side chain to be modified (step (iii)), or it may be washed, e.g. with dichloromethane, prior to the TFA/DCM treatment. It is important to note that it is not required to swell the shrunken resin prior to application of TFA/DCM. The inventors found that at this stage of the synthesis of the final peptide, there is an upscaling effect, i.e. the amount of undesired side products, which do not possess the intended lysine modification, is increased above average when the molar scale of the synthesis is increased. Surprisingly, the negative impact of this upscaling effect could be lessened depending on the number of repetitions of step (iii). Accordingly, in certain preferred embodiments of the invention, the resin-bound peptide is treated at least five times, particularly 7, 8, 9 or 10 times with a solution of TFA in DCM. The time of each treatment is at least five minutes, particularly at least 10 minutes. The concentration of TFA in DCM is between 0.5 to 1.5% (v/v), particularly about 1% (v/v), more particularly 1% (v/v). Selecting these concentrations has certain advantageous effects, in particular for the synthesis of peptides containing more than one lysine residue. With higher concentrations of TFA, e.g. 2% TFA in DCM, not only Mmt- or Mtt-protection groups are cleaved, but also partially other protecting groups used for lysine, e.g. Boc, especially when performing several (e.g. 6-12) repetitions, thereby causing unwanted multiple acylations of different lysines in the peptide chain. This can be avoided by keeping TFA concentrations between 0.5 and 1.5% (v/v).

"Resin-bound peptide" in the context of the present invention refers to a resin suitable for solid phase peptide synthesis, to which a peptide according to the invention is covalently bound.

In certain preferred embodiments, the resin-bound peptide is treated at least seven times for at least 5 minutes, particularly nine times for at least 10 minutes or nine times for at least 15 minutes, with a solution of about 1% (v/v) TFA in DCM. According to one embodiment, the treatment is performed nine times for 10 minutes with 1% (v/v) TFA in DCM.

The number of treatment steps with TFA in DCM may particularly be selected depending on the scale of the synthesis. For example, for scales up to 10 mmol, five treatments with about 1% TFA in DCM are sufficient. For scales≥50 mmol, at least five treatments may be carried out. For scales≥100 mmol, at least seven treatments may be carried out. For scales≥500 mmol, at least nine treatments may be carried out. As an example, for a scale of 800 mmol, nine treatments for 10 minutes with 1% (v/v) TFA in DCM may be performed.

Given the low boiling point of DCM, the temperature during the treatment step is set below this point. Advantageously, treatment is started with resin-bound peptide chilled to about 0° C., e.g. 0-5° C. During the TFA/DCM treatment, the temperature may rise up to 25° C. In exemplary embodiments, the first treatment steps are carried out at a temperature range of between 0 and 5° C., later treatment steps are carried out at a temperature of between 5 and 15° C., and the final treatment steps are carried out at a temperature of between 15 and 25° C. For example, when nine treatment steps with TFA/DCM are carried out, three of them may be performed at 0-5° C., three at 5-15° C. and three at 15-25° C.

Once the TFA/DCM treatment is completed, the resin-bound peptide may be washed, e.g. with DCM. Subsequently, the resin-bound peptide is neutralized (step (iv)). The resin-bound peptide is considered sufficiently neutralized once a pH of ≥7, particularly ≥7.5, more particularly ≥8.0 is reached.

Neutralization is achieved by at least one incubation of the resin-bound peptide with a 1%-5% solution of a tertiary alkylamine in an organic polar aprotic solvent. Suitable neutralization solutions for use in the present application are diisopropyl ethylamine (DIPEA) in dichloromethane or N-methylmorpholine (NMM) in dichloromethane or triethylamine in dichloromethane. In particular, a solution of 2%-4%, more particularly a 3% (v/v) solution of DIPEA in DCM may be used.

Neutralization is carried out at least once, particularly for at least 10 minutes, optionally followed by determination of the pH of the solvent mixture after the neutralization step. It was surprisingly found that neutralization is required for a good yield in the subsequent coupling reaction, in particular for larger scales. It was further surprisingly found that the residual TFA present in the resin is usually not sufficiently neutralized with one incubation in neutralizing solution. Therefore, if the pH of the solvent mixture after the first incubation is too acidic, at least one further incubation with neutralization solution is carried out. In certain embodiments, more than two incubations of the resin-bound peptide with the neutralization solution is performed, e.g. 3 incubations, particularly 5 incubations, e.g. with 3% DIPEA in DCM. In some embodiments, 6 incubations with the neutralization solution, e.g. 3% DIPEA in DCM, are performed.

In exemplary embodiments, neutralization is carried out at a temperature range of between 0 and 25° C. It is possible to maintain the temperature at a specific narrow range or to gradually increase temperature. For example, when more than one neutralization step is carried out, the first neutralization may be performed at a temperature of between 0 and 5° C., whereas subsequent neutralization incubations are carried out at a temperature of between 5 and 15° C. or even between 15 and 25° C.

Following neutralization, the peptide on resin is washed at least once with the organic polar aprotic solvent used in the neutralization (without base), and at least once with a further polar aprotic solvent, e.g. dimethylformamide (DMF). DMF is particularly used when subsequent coupling involves using HBTU and DIPEA. Washing with the further solvent is particularly performed more than once, e.g. 3 times.

In the next synthesis step of the peptide of interest, at least one 9-fluorenylmethyloxycarbonyl (Fmoc)-bound linker moiety is activated according to standard procedure, and coupled to the deprotected lysine side chain (step (v)).

A "linker moiety" according to the present invention generally is a linear short-chain molecule having functional groups suitable for binding to the free amino side chain group of the deprotected lysine on one end and to the free functional group of the lipophilic moiety (e.g. the carboxy group of a fatty acid) on the other end. Particularly, the linker moiety is a $C_1$-$C_{10}$ alkyl chain containing terminal functional groups (i.e. one functional group at each end) independently selected from amino and carboxy, wherein one, two or three of the carbon atoms in the alkyl chain may be replaced by oxygen. Non-limiting examples of the "linker moiety" according to the present invention are naturally occurring and non-naturally occurring amino acids, particularly β-alanine (β-Ala), γ-glutamic acid (γE), γ-aminobutyric acid (GABA), amino-ethoxy-ethoxy acetic acid (AEEAc) and ε-aminohexanoic acid (EACA) in all their stereoisomeric forms.

The complete linker between the lysine side chain and the lipophilic group may consist of one or more of such linker moieties, particularly one, two or three identical or different linker moieties. In certain embodiments, the complete linker consists of one, two or three linker moieties independently selected from β-Ala, γE, GABA, AEEAc and EACA. Specific examples of complete linkers are β-Ala, γE, GABA, AEEAc, EACA, β-Ala-β-Ala, γE-γE, γE-γE-γE, AEEAc- AEEAc-γE, and AEEAc-AEEAc-AEEAc. In certain preferred embodiments, the linker is γE.

The functional group of the linker to which the lipophilic moiety is to be coupled (i.e. the terminal functional group not coupled to the lysine side chain) is protected by Fmoc. In certain embodiments, the Fmoc-bound linker moiety is Fmoc-Glu-OtBu. In an exemplary embodiment, Fmoc-Glu-OtBu is activated with 3 equivalents 2-(1H-Benzotriazole-1-yl)-1,1,3,3-tetramethylaminium hexafluorophosphate (HBTU) and 6 equivalents DIPEA in DMF or O-(7-Azabenzotriazol-1-yl)-N,N,N',N'-tetramethyluronium hexafluorphosphate (HATU) and 6 equivalents DIPEA in DMF.

The coupling mixture is added to the resin with the deprotected lysine side chain and incubated for a sufficient amount of time, e.g. 3-4 hours. The incubation is particularly carried out with stirring (e.g. at 30-100 rpm). After completion of the coupling, the coupling mixture is removed from the resin, and the resin-bound peptide is washed with the solvent used for coupling, e.g. DMF. If the complete linker consists of more than one linker moiety, the coupling is repeated after deprotection of the first linker moiety.

In subsequent step (vi), the terminal functional group of the linker coupled to the lysine side chain in step (v) is deprotected. Deprotection conditions for Fmoc are generally known to the skilled person. Deprotection in step (vi) may, in certain embodiments, be performed by treating the peptide on resin at least once for at least 5 minutes with a base, followed by at least one washing step. In particular embodiments of the invention, Fmoc-deprotection may be carried out by at least one treatment with piperidine at a suitable concentration, e.g. 20% piperidine in DMF. Particularly, deprotection is performed in two incubation steps, e.g. 5 and 20 minutes, using 20% piperidine in DMF. After completion of deprotection, the resin-bound peptide is washed at least once with the solvent before proceeding further.

Next, the lipophilic moiety is activated to prepare its coupling to the deprotected linker, e.g. by incubation with hydroxybenzotriazol hydrate (HOBt Hydrate) and diisopropyl carbodiimide (DIC). In certain embodiments, activation is done by incubating the lipophilic moiety to be used with equivalent amounts of HOBt hydrate and DIC for e.g. 10 minutes in DMF.

Suitable "lipophilic moieties" according to the present invention are in particular fatty acids. Among fatty acids, particularly palmitic acid, stearic acid and myristic acid may be advantageously used in the present invention. In particular embodiments, palmitic acid is selected as the lipophilic moiety. In certain preferred embodiments, palmitic acid is coupled to Lys(14) of the resin-bound peptide via γE.

The preactivated lipophilic moiety, particularly a preactivated fatty acid, is then added to the resin-bound peptide. The coupling of the activated lipophilic moiety to the deprotected terminal functional group of the linker, i.e. step (vii) of the method according to the invention, proceeds for at least 2 hours, particularly from 4 to 22 hours. In particular embodiments, an activated fatty acid, e.g. palmitic acid, is added to the resin-bound peptide having a deprotected amino group as the terminal functional group of the linker and coupled using HOBt hydrate/DIC. In certain preferred embodiments, the linker having the deprotected amino group is γE.

After completion of coupling, the coupling solution is removed from the resin, and the resin is washed at least once with the solvent of the coupling step. Further washes with different solvents may be carried out as well. In particular embodiments, the resin-bound peptide is washed at least once with the solvent used for coupling, e.g. DMF, at least once with an aliphatic alcohol, e.g. methanol, ethanol, n-propanol or isopropanol (IPA), and at least once with a dialkyl ether, e.g. diethyl ether, tert.butylmethyl ether, diisopropyl ether (DIPE) or diisobutyl ether. In an exemplary embodiment, the following washes are carried out: two times DMF, three times IPA, three times DIPE. In a further exemplary embodiment, the following washes are carried out: three times DMF, three times IPA, three times DIPE.

The washed peptide on resin is, in the next step (step (viii)), dried. Drying of the resin may, in certain embodiments, be performed under vacuum. In other embodiments, drying is performed under inert gas, e.g. in a continuous nitrogen stream (stripping nitrogen).

After completion of step (viii), the peptide is ready to be cleaved from the resin, which is done in step (ix) of the method according to the invention.

In order to be sure that a sufficient percentage of the peptide bears the desired lipophilic modification, in certain embodiments it is not directly proceeded to the cleavage reaction. Rather, in these embodiments an "in process control" is done. Accordingly, in these embodiments, after the resin-bound peptide has been dried in step (viii) of the inventive method, the deprotection yield of step (iii) is analyzed by cleaving a test sample of the resin-bound peptide (step (viii-a)).

In certain embodiments, analyzing the deprotection yield may comprise
(viii-a1) removing a test sample of the resin from the total reaction batch and cleaving the peptide from the test sample under the same conditions and with the same cleavage cocktail as in step (ix); and
(viii-a2) determining the content of cleaved peptide containing the modified lysine side chain in comparison to the peptide without modified lysine side chain, in particular by high pressure liquid chromatography (HPLC) or a combination of HPLC and mass spectrometry (LC-MS).

The test sample will be small as compared to the total reaction batch. A sample size of not more than 0.1% of the total reaction batch will usually be sufficient.

Depending on the result of the analysis in step (viii-a), steps (iii) to (viii-a) are optionally repeated until the content of cleaved peptide containing the modified lysine side chain is sufficient. A sufficient content of cleaved peptide containing the modified lysine side chain may be at least 85%, particularly at least 90%, more particularly at least 95%, or even >95%, e.g. 96, 97, 98 or 99%, compared to peptide without modified lysine side chain. For example, if a first test cleavage shows a content of modified lysine side chain of 50%, a reprocessing (i.e. reiterating steps (iii) to (viii-a)) is advantageous to increase yield. If, after the reprocessing, the content of modified lysine side chain is for example above 85%, it is possible to proceed to step (ix), i.e. cleavage of the bulk peptide from the resin. If, on the other hand, reprocessing yields only an increase in the content of modified lysine side chain to e.g. 60%, further reprocessing is indicated. By introducing the IPC combined with reprocessing, the method of the invention becomes independent of upscaling effects, as the synthesis steps can be repeated or adjusted to optimize yield and/or purity of the product.

Therefore, in certain preferred embodiments of the invention, Mmt cleavage is performed with 1% TFA in DCM nine times for at least 10 minutes, neutralization is performed with pH control, and reprocessing, in particular for bigger scales, is applied.

It was found that one particular measure to increase yield and/or purity of the desired peptide with modified lysine side chain is adjusting the number of treatments with TFA in DCM in step (iii) of the inventive method. If, for example, the content of modified lysine side chain in the peptide of interest is too low, the number of TFA/DCM-treatments may be increased. The number of TFA in DCM treatments in step (iii) is particularly adjusted such that the yield of modified lysine side chain in step (ix) is at least 85%, particularly at least 90%, more particularly at least 95%, or even >95%, e.g. 96, 97, 98 or 99%.

Once the test cleavage gives the desired result (i.e. only a minimal amount of side product with unmodified lysine side chain), or, in case no test cleavage is performed, directly after step (viii), cleavage of the peptide from the resin is carried out. In the context of the present invention, cleavage is preferably carried out using a specifically developed cleavage cocktail, which has advantages as compared to the conventionally used King's Cocktail (King et al., Int. J. Peptide Protein Res. 36, 255-266, 1990), comprising trifluoroacetic acid (TFA), phenol, water, thioanisole and 1,2-ethanedithiol (EDT).

It was found that better yield, higher content and better purity of the cleaved peptide can be achieved when using cleavage cocktails which are free of thioanisole and ethylmethylsulfide. In particular, suitable cleavage cocktails according to the invention comprise at least 90% (v/v) trifluoroacetic acid and at least 1% (v/v) ethanedithiol, and are free of thioanisole and ethylmethylsulfide. Further suitable cleavage cocktails of the invention are free of thioanisole and ethylmethylsulfide and comprise at least 80% (w/w) trifluoroacetic acid and at least 1% (w/w) 1,2-ethanedithiol. In the context of the present invention, calculations regarding the density have been carried out with a value of 1.53 g/cm$^3$ (at 20° C.) for trifluoroacetic acid and 1.12 g/cm$^3$ (at 20° C.) for 1,2-ethanedithiol. For example, these values can be used to calculate the mass of TFA or EDT from a given volume, e.g. to calculate weight to weight (w/w) ratios.

In exemplary embodiments, a cleavage cocktail consisting of 91-93% (v/v) trifluoroacetic acid, 1-6% (v/v) phenol and 1-8% (v/v) ethanedithiol is used. In other embodiments, a cleavage cocktail consisting of 96-98% (v/v) trifluoroacetic acid and 2-4% (v/v) ethanedithiol is used.

Specific exemplary cleavage cocktails according to the invention are (i) a solution consisting of about 92.2% (v/v) trifluoroacetic acid, about 5.1% (v/v) phenol and about 2.7% (v/v) ethanedithiol and (ii) a solution consisting of about 97.1% (v/v) trifluoroacetic acid and about 2.9% (v/v) ethanedithiol.

In addition, it has been found by the present inventors that the use of a suitable indole compound as a supplemental scavenger can further improve the claimed method, because it aids in efficiently suppressing occurrence of a particular undesired side product, formed by a degradation product of the Rink linker and a tryptophane residue of the peptide during cleavage of the peptide from the resin. Ogawa et al. (Chem. Pharm. Bull. 26(10) 3144-3149 (1978)) mention the use of 3-methylindole to suppress side reactions during the treatment of Z(OMe)-Trp-OH or Boc-Trp-OH with TFA. However, 3-methylindole is only used as part of a scavenger system together with anisole and EDT, thioanisole and EDT or dimethylsulfide and EDT. Suitable indole compounds according to the present invention are those that efficiently scavenge the above-mentioned undesired side product. For example, suitable indole compounds may be indoles carrying a lower ($C_1$-$C_3$) alkyl or lower acyl ($C_1$-$C_3$) substituent at the carbon atom C3 or at the nitrogen atom, particularly N-acetylindole and 3-methylindole (also known as skatole). In certain embodiments, 3-methylindole is used as the indole compound.

Accordingly, further suitable cleavage cocktails of the invention are free of thioanisole and ethylmethylsulfide and comprise at least 90% (w/w) trifluoroacetic acid, at least 1% (w/w) 1,2-ethanedithiol and at least 0.5% (w/w) of a suitable indole compound, e.g. 3-methylindole. In further exemplary embodiments, a cleavage cocktail consisting of 88.2-98.3% (w/w) trifluoroacetic acid (TFA), 1-4.3% (w/w) 1,2-ethanedithiol (EDT) and 0.7-7.5% (w/w) 3-methylindole (3-MI), particularly consisting of 96.0-97.5% (w/w) TFA, 1.7-2.6% (w/w) EDT and 0.7-1.5% (w/w) 3-methylindole is used.

Further exemplary cleavage cocktails according to the invention are (iii) a solution consisting of about 97% (w/w) TFA, about 2% (w/w) EDT and about 1% 3-MI and (iv) a solution consisting of about 96.9% (w/w) TFA, about 2.3% (w/w) EDT and about 0.8% 3-MI.

Cleavage of the peptide from the resin can be carried out over a relatively broad temperature range. In particular, cleavage may be performed at 5-15° C., 15-22° C. and/or 22-30° C., particularly at 25° C. In certain embodiments, cleavage is performed at room temperature (18-24° C.). Incubation time is preferably as short as possible. Usually, incubation of about 4 hours, particularly 4 hours at room temperature is sufficient to obtain acceptable cleavage. However, in certain preferred embodiments of the invention, the cleavage time can be reduced to only 2 hours, when performing the cleavage reaction at 25° C., which has the advantage that the peptide exposition to TFA is considerably reduced. It was surprisingly found that despite the increase in temperature, the formation of unwanted isomers is not significantly increased. In exemplary embodiments, cleavage is performed for 2-3 hours, in particular for 2-3 hours or 2.0-2.5 hours at 25° C., with stirring (at e.g. 30-100 rpm). In other embodiments, cleavage is performed for 1-1.5 hours at 30° C., with stirring (at e.g. 30-100 rpm).

In addition or alternatively, the volume of the cleavage cocktail per gram of peptide on resin may be adjusted to facilitate later processing and purification. It was surprisingly found that it is possible to reduce the volume of the cleavage cocktail as compared to conventional procedure by at least 10%, in particular by at least 20% und up to 30%. Taking into account a standard volume of King's Cocktail of about 9 ml/g, e.g. 9.2 ml/g, the volume could be reduced by about 24% in exemplary embodiments. On a quantitative scale, this means that the volume of the cleavage cocktail per gram of peptide on resin may for example be from 9.5 ml to 5.5 ml, particularly from 7.0 ml to 6.0 ml.

In certain embodiments, cleavage according to step (ix) of the inventive method is performed using
(a) a cleavage cocktail consisting of 91-93% (v/v) trifluoroacetic acid, 1-6% (v/v) phenol and 1-8% (v/v) ethanedithiol, e.g. about 92.2% (v/v) TFA, about 5.1% (v/v) phenol and about 2.7% EDT,
(b) an incubation time of 2.0-2.5 hours at an elevated temperature of 25° C., and
(c) a reduced volume of cleavage cocktail per gram peptide-on-resin, e.g. 7.0 ml to 6.0 ml.

In certain preferred embodiments, cleavage according to step (ix) of the inventive method is performed using
(a) a cleavage cocktail consisting of 91-93% (v/v) trifluoroacetic acid, 1-6% (v/v) phenol and 1-8% (v/v) ethanedithiol, e.g. about 92.2% (v/v) TFA, about 5.1% (v/v) phenol and about 2.7% EDT,
(b) an incubation time of only 2 hours at an elevated temperature of 25° C., and
(c) a reduced volume of cleavage cocktail per gram peptide-on-resin, e.g. 7.0 ml to 6.0 ml.

In other embodiments, cleavage according to step (ix) of the inventive method is performed using
(a) a cleavage cocktail consisting of 96-98% (v/v) trifluoroacetic acid and 2-4% (v/v) ethanedithiol, e.g. about 97.1% (v/v) TFA and about 2.9% (v/v) EDT,
(b) an incubation time of 2.0-2.5 hours at an elevated temperature of 25° C., and
(c) a reduced volume of cleavage cocktail per gram peptide-on-resin, e.g. between 7.0 ml and 6.0 ml.

In other preferred embodiments, cleavage according to step (ix) of the inventive method is performed using
(a) a cleavage cocktail consisting of 96-98% (v/v) trifluoroacetic acid and 2-4% (v/v) ethanedithiol, e.g. about 97.1% (v/v) TFA and about 2.9% (v/v) EDT,
(b) an incubation time of only 2 hours at an elevated temperature of 25° C., and
(c) a reduced volume of cleavage cocktail per gram peptide-on-resin, e.g. between 7.0 ml and 6.0 ml.

In yet other preferred embodiments, cleavage according to step (ix) of the inventive method is performed using
(a) a cleavage cocktail consisting of 88.2-98.3% (w/w) trifluoroacetic acid, 1-4.3% (w/w) 1,2-ethanedithiol and 0.7-7.5% (w/w) 3-methylindole, particularly consisting of 96.0-97.5% (w/w) TFA, 1.7-2.6% (w/w) EDT and 0.7-1.5% (w/w) 3-MI, e.g. about 97% (w/w) TFA, about 2% (w/w) EDT and about 1% 3-MI,
(b) an incubation time of only 2.0-2.5 hours at an elevated temperature of 25° C., and
(c) a reduced volume of cleavage cocktail per gram peptide-on-resin, e.g. between 7.0 ml and 6.0 ml.

In some embodiments, the inventive method comprises additional steps after cleaving the peptide from the resin, i.e.:
(x) filtering the peptide solution after cleavage;
(xi) distilling the filtered peptide solution under vacuum;
(xii) adding the residual fraction from the distillation to an antisolvent comprising a dialkyl ether and a heptane;
(xiii) stirring the precipitated solution
(xiv) filtering the precipitated solution;
(xv) washing the precipitate; and
(xvi) drying the wet peptide.

These steps aid in the further purification of the peptide of interest. First of all, filtration (step (x)) of the cleavage product of step (ix) allows separation of the lipophilically modified peptide from the solid support. Filtration is usually carried out at room temperature. The remaining filter cake is rinsed at least once with a suitable rinsing solution to completely recover residual peptide from the solid support. A suitable rinsing solution according to the invention is trifluoroacetic acid. The filter cake may be rinsed once to five times, particularly three times with TFA.

The collected filtrate fractions (filtrate from first filtration and filtrates from rinsing the filter cake) are pooled and subjected to a distillation under vacuum in step (xi) in order to reduce volume. In some embodiments, the vacuum applied is ≤50 mbar, and the distillation temperature is ≤30° C. In an exemplary embodiment, the solution is distilled for about 1 to about 2.5 hours, e.g. 1.5-2 hours. Distillation reduces the volume of the peptide-containing solution to about one third of the volume before precipitation. The peptide remains in the residual fraction, the distillate contains mainly TFA.

Subsequently to distillation, the concentrated peptide-containing solution is added to an antisolvent comprising a dialkyl ether and a heptane (step (xii)). In some embodiments, the antisolvent is a mixture consisting of diisopropyl ether (DIPE) and n-heptane. The ratio of DIPE to n-heptane may e.g. be in the range of from 25:75 to 35:65 (v/v). In exemplary embodiments, the ratio DIPE/n-heptane is 25:75 (v/v) or 30:70 (v/v) or 35:65 (v/v).

The vessel from which the concentrated peptide-containing solution is transferred is usually rinsed once with a suitable solvent, e.g. TFA, to maximise yield.

In certain embodiments, the antisolvent is pre-cooled to about 0-5° C. To this pre-cooled antisolvent, the peptide-containing solution is, according to some embodiments, added over a period of about 20 to about 60 minutes.

The antisolvent is required to precipitate the peptide of interest from the peptide-containing solution. Precipitation is also possible when using just a dialkyl ether. However, the present inventors have surprisingly found that an antisolvent containing in particular n-heptane advantageously influences the time required for subsequent filtration. For example, by using a mixture of DIPE/n-heptane in the range of 25:75 (v(v) to 35:65 (v/v), the filtration time after precipitation can be reduced by a factor of up to about 60 as compared to using DIPE alone as an antisolvent (see Examples).

After addition of the peptide-containing solution to the antisolvent is completed, the resulting peptide suspension is tempered, e.g. to about 10-15° C. Subsequently, the precipitate is aged (step (xiii)), i.e. it is stirred at e.g. 20-30 rpm and a temperature of e.g. 10-15° C. for a certain amount of time. For example, aging is carried out for 1-20 hours, e.g. 2-18 hours or 10-20 hours.

Upon completion of the aging step (xiii), the precipitated solution is subjected to a filtration (step (xiv)) in order to separate the desired peptide, i.e. the precipitate, from the mother liquor consisting mainly of DIPE, heptane and TFA. The precipitate on the filter may then be rinsed with a suitable organic solvent, e.g. ethyl acetate.

Subsequently, the precipitate on the filter is washed at least once (step (xv)). In certain embodiments, washing the precipitate on the filter comprises (xv-a) resuspending the precipitate in a suitable organic solvent, (xv-b) stirring the resulting suspension, and (xv-c) filtering off the organic solvent. An exemplary organic solvent is ethyl acetate. Stirring may be carried out for e.g. 30-60 minutes. In some embodiments, the precipitate is washed at least twice, or at least three times. In certain embodiments, the precipitate is washed 1-5 times, particularly 2-4 times or 3-5 times or 4-5 times with ethyl acetate.

After the washing solution of the last wash has been filtered off, the precipitate, i.e. the crude, wet peptide of interest, is dried. Drying may carried out under vacuum, e.g., at 20 to 25° C. In some embodiments, drying is carried out under a vacuum of ≤70 mbar at 20 to 25° C. and nitrogen stripping.

The isolated peptide according to the invention comprising a lipophilically modified lysine side chain is particularly an exendin-4 derivative having a length of between 30 and 44, more particularly between 38 and 40 amino acids, more particularly 39 amino acids, wherein preferably (i) the sequence identity to wild-type exendin-4 in the region corresponding to amino acids 1-13 of wild-type exendin is at least 65%, and/or (ii) the sequence identity to wild-type exendin-4 in the region corresponding to amino acids 22-39 of wild-type exendin is at least 70%, and/or (iii) the lipophilically modified lysine side chain is at position 14 (Lys (14)) with respect to the amino acid positions of wild-type exendin-4.

For illustration purposes, the assignment of amino acid positions of wild-type exendin-4 (SEQ ID NO.: 3) is provided as follows:

```
 1  2  3  4  5  6  7  8  9 10 11 12 13 14 15 16 17 18 19 20 21 22 23
 H  G  E  G  T  F  T  S  D  L  S  K  Q  M  E  E  E  A  V  R  L  F  I 24 25 26 27 28 29 30 31 32 33 34 35 36 37 38 39
 E  W  L  K  N  G  P  S  S  G  A  P  P  P  S-NH₂
```

An identity of at least 65% in the region corresponding to amino acids 1-13 of wild-type (wt) exendin-4 means that a maximum of 4 amino acids is substituted as compared to wild-type exendin-4. In particular, positions suitable for mutations in this region are positions 1, 2, 3, 10, 12 and 13. In certain preferred embodiments, the region corresponding to amino acids 1-13 of wild-type (wt) exendin-4 contains mutations in positions 2 and 3. In certain preferred embodiments, the mutations are Gly2D-Ser (i.e. a mutation from glycine to D-serine at position 2) and Glu3Gln (i.e. a mutation from glutamate to glutamine at position 3).

An identity of at least 70% in the region corresponding to amino acids 22-39 of wt exendin-4 means that a maximum of 5 amino acids is substituted as compared to wt exendin-4. In particular, positions suitable for mutations in this region are, according to the invention positions 23, 24, 27, 28, 29 and 35. In certain preferred embodiments, the region corresponding to amino acids 22-39 of wild-type (wt) exendin-4 contains a mutation in position 28. In certain preferred embodiments, the mutation is Ala28Asn (i.e. a mutation from alanine to asparagine at position 28).

In certain preferred embodiments, the isolated peptide is an exendin-4 derivative and contains only one modified lysine side chain. This single modified lysine is in particular located at position 14 with respect to the amino acid positions of wild-type exendin-4.

In particular embodiments, the isolated peptide has a length of 39 amino acids, the sequence identity to wild-type exendin-4 in the region corresponding to amino acids 1-13 of wild-type exendin is at least 65%, the sequence identity to wild-type exendin-4 in the region corresponding to amino acids 22-39 of wild-type exendin is at least 70%, and the lipophilically modified lysine side chain is at position 14 (Lys(14)) with respect to the amino acid positions of wild-type exendin-4.

In further embodiments, the isolated peptide has a length of 39 amino acids, the sequence identity to wild-type exendin-4 in the region corresponding to amino acids 1-13 of wild-type exendin is at least 80% (i.e. contains no more than 2 mutations), the sequence identity to wild-type exendin-4 in the region corresponding to amino acids 22-39 of wild-type exendin is at least 90% (i.e. contains no more than one mutation), and the lipophilically modified lysine side chain is at position 14 (Lys(14)) with respect to the amino acid positions of wild-type exendin-4. In certain preferred embodiments, the isolated peptide of the invention contains exactly two mutations in the region corresponding to amino acids 1-13 of wild-type exendin, contains exactly one mutation in the region corresponding to amino acids 22-39 of wild-type exendin, and the lipophilically modified lysine side chain is at position 14 (Lys(14)), each with respect to the amino acid positions of wild-type exendin-4.

In certain preferred embodiments, the isolated peptide has the amino acid sequence H-dS-Q-G-T-F-T-S-D-L-S-K-Q-K(γE-Palm)-E-S-K-A-A-Q-D-F-I-E-W-L-K-A-G-G-P-S-S-G-A-P-P-P-S-NH₂ (SEQ ID NO.: 1). "γE-Palm" in the context of the present invention represents a (S)-4-carboxy-4-hexadecanoyl aminobutyryl moiety, and "dS" stands for D-Ser.

The invention is further illustrated by the following examples.

EXAMPLES

Example 1: Solid Phase Peptide Synthesis Using Rink Amide Resin

In a first Example, the amino acid sequence of SEQ ID NO: 1 was synthesized via SPPS using Rink amide resin and Fmoc strategy.

Loading of the Resin:

The solid phase synthesis was started with Rink amide Resin (4-[(2,4-Dimethoxyphenyl)(Fmoc-amino)methyl] phenoxy acetamido methyl resin) which was deprotected twice (5 and 20 minutes) with 20% piperidine in DMF. The loading of the resin may be in the range of 0.2-0.9 mmol/g. The resin was washed thoroughly with DMF. Then Fmoc-Ser(tBu)-OH was coupled onto the liberated amino group on the Rink-resin using the coupling reagents HOBt Hydrate and DIC in DMF which are used in equimolar amounts to the Fmoc-amino acid. The coupling time may range from 18-22 h. Hereafter the resin was washed again with DMF several times.

Peptide Assembly of the Linear Chain:

After the first Fmoc-amino acid was coupled onto the resin, the Fmoc-group was removed again with 20% piperidine in DMF (5 and 20 minutes) followed by thorough washings with DMF and by the coupling of the next Fmoc-amino derivative which is Fmoc-Pro-OH using again HOBt Hydrate and DIC in DMF as coupling reagents. In repetitive cycles the linear sequence was synthesized up to position 2 where Fmoc-D-Ser(tBu)-OH is used. The coupling times range from 2 to 22 h, the equivalents of building blocks and coupling reagents range from 2 to 3.5. For the positions 37/36 the dipeptide Fmoc-Pro-Pro-OH was employed. For position 1, Boc-His(Trt)-OH was coupled. The coupling and deprotection steps as well as the washing steps can be performed in a temperature range from 10° C. to 40° C.

The following Fmoc-amino acid derivatives were applied: Fmoc-Ser(tBu)-OH for positions 39, 33, 32, 16, 11, 8; Fmoc-Pro-OH for positions 38 and 31; Fmoc-Pro-Pro-OH for the positions 37 and 36; Fmoc-Ala-OH for the positions 35, 19, 18; Fmoc-Gly-OH for the positions 34, 30, 29, 4; Fmoc-Lys(Boc)-OH for the positions 27, 17, 12; Fmoc-Leu-OH for the positions 26, 10; Fmoc-Trp(Boc)-OH for the position 25; Fmoc-Glu(OtBu)-OH for the positions 24, 15; Fmoc-Ile-OH for the position 23; Fmoc-Phe-OH for the positions 22, 6; FmocAsp(OtBu)-OH for the positions 21, 9; Fmoc-Gln(Trt)-OH for the positions 20, 13, 3; Fmoc-Lys(Mmt)-OH or alternatively Fmoc-Lys(Mtt)-OH for the position 14; Fmoc-Thr(tBu)-OH for the positions 7, 5; Fmoc-D-Ser(tBu)-OH for position 2; Boc-His(Trt)-OH for position 1.

Example 2: Modification of the Lys(14) Side-Chain

The peptide of Example 1 was further modified at position 14, where according to the invention a lipophilic moiety is attached. Surprisingly, it was found that an upscale effect is observed regarding the Mmt cleavage.

Treatment of the Resin-Bound Peptide with TFA/DCM:

The selective and complete removal of the Mmt-group (Monomethoxytrityl) from the side-chain of Lys(14) is one of the core parts in this description. The cleavage was performed with 1% TFA in dichloromethane (DCM) on lab scale (8 mmol). For the cleavage of the Mmt-group the resin was washed with DCM and treated 3 times with 1% TFA in DCM. Thereafter Fmoc-Glu-OtBu was coupled onto the liberated amino-group in a 3 fold excess using 3 equivalents (eq) HBTU and 6 eq DIPEA in DMF. After several washes with DMF, the Fmoc-group was cleaved, the resin was washed again and palmitic acid was coupled using HOBt Hydrate and DIC. Afterwards the peptide was cleaved from the resin with King's Cocktail and analysed by HPLC. The desired product SEQ ID NO: 1 was found together with 4.3% of SEQ ID NO:2, where the side-chain at Lys(14) was missing.

```
                                                    SEQ ID NO: 2
H-dS-Q-G-T-F-T-S-D-L-S-K-Q-K-E-S-K-A-A-Q-D-F-I-E-
W-L-K-A-G-G-P-S-S-G-A-P-P-P-S-NH2
```

The occurrence of 4.3% of SEQ ID NO: 2 can be explained by an incomplete removal of the Mmt-group.

The solid-phase synthesis was repeated on a 36 mmol scale with the same protocol and it was surprisingly found that the amount of SEQ ID NO: 2 increased to 12.6%. For the next synthesis already on pilot scale (800 mmol) 5 treatments with 1% TFA in DCM were applied and 28.7% of SEQ ID NO: 2 were detected.

These unexpected results are due to an upscaling effect.

TABLE 1

Increase in undesired side product SEQ ID NO: 2 depending on the scale of the reaction (upscaling effect)

|  | Reaction scale | | |
| --- | --- | --- | --- |
|  | 8 mmol | 36 mmol | 800 mmol |
| Percentage of SEQ ID NO: 2 | 4.3% | 12.6% | 28.7% |
| Procedure for Mmt-cleavage | 3 × 1% TFA/DCM | 3 × 1% TFA/DCM | 5 × 1% TFA/DCM |

Several further attempts were undertaken to improve the cleavage efficiency of the Mmt-group. The cleavage steps were increased to 7 treatments which led to a percentage of SEQ ID NO: 2 of 15.7% (scale=800 mmol).

In a next trial the resin was dried prior to the treatment with 1% TFA in DCM. Therefore the linear peptide on resin was washed 3 times with isopropanol and 3 times with diisopropyl ether and dried under a nitrogen purge for >16 h. Hereafter the resin was treated directly with 1% TFA in DCM for 7 times followed by one DCM-wash and neutralization steps that were performed with 3% DIPEA in DCM until pH>8. The coupling of Fmoc-Glu-OtBu and palmitic acid was performed as already described. After cleavage of the peptide from the resin a crude product was obtained with a percentage of SEQ ID NO: 2 of 12.5% (scale=680 mmol).

Furthermore, the cleavage of the Mmt-group was performed 8 times with the application of the predrying steps as mentioned before. After cleavage of the peptide from the resin a crude product was obtained with a percentage of SEQ ID NO: 2 of 8.4% (scale=680 mmol).

Next, the cleavage was performed 9 times with the application of the predrying steps as mentioned before. After cleavage of the peptide from the resin a crude product was obtained with a percentage of SEQ ID NO: 2 of 3.6% (scale=680 mmol).

TABLE 2

Reduction of the upscaling effect by predrying the resin (step (ii)), increasing the number of treatments with TFA/DCM (step (iii)), and neutralizing the peptide-bound resin before further work-up

|  | 800 mmol | 680 mmol | 680 mmol | 680 mmol |
| --- | --- | --- | --- | --- |
| Percentage of SEQ ID NO: 2 | 15.7% | 12.5% | 8.4% | 3.6% |
| Procedure for Mmt-cleavage | 7 × 1% TFA/DCM | 7 × 1% TFA/DCM, predrying, neutralization | 8 × 1% TFA/DCM, predrying, neutralization | 9 × 1% TFA/DCM, predrying, neutralization |

Accordingly, the best results were achieved with a combination of predrying, nine treatments with TFA/DCM and subsequent neutralization.

Reprocessing Step:

In order to be independent from further upscaling effects if the scale is to be increased further (i.e. to >800 mmol, maybe 4000-5000 mmol), a reprocessing step could be established. Therefore a test cleavage of SEQ ID NO: 1 from the resin (1 g) will be executed leading to a crude peptide with a certain amount of SEQ ID NO: 2. Depending on the percentage of SEQ ID NO: 2 a reprocessing step might be performed. To this end, the dried peptide on resin was treated 5 times with 1% TFA in DCM, neutralized with 3% DIPEA in DCM until pH>8 was reached, washed with DCM and several times with DMF. Then the coupling of Fmoc-Glu-OtBu (3 eq) was carried out with the coupling reagents HBTU (3 eq) and DIPEA (6 eq). After the coupling was complete, the Fmoc-group was removed as described before and palmitic acid was coupled using HOBt Hydrate and DIC.

The following workflow shows the principal procedure for the Mmt-cleavage with subsequent couplings without reprocessing.

a) After coupling of the N-terminal amino acid (Boc-His(Trt)-OH) the resin is washed twice with dimethylformamide (DMF).
b) Resin is washed 3 times with isopropanol (IPA) and diisopropyl ether (DIPE), resin shrinks.
c) Resin is dried via a continuous nitrogen stream for several hours preferably overnight.
d) Resin is treated 9 times with TFA (1% in DCM) for 10 minutes each
e) Washing of resin with DCM
f) Several neutralization steps by treating resin with diisopropylethyl amine (DIPEA, 3% in DCM) for 10 minutes each, pH-control of washing solution, end point: pH>8
g) Washes with DCM (1×) and DMF (3×)
h) Activation of 3 eq Fmoc-Glu-OtBu with 3 eq 2-(1H-Benzotriazole-1-yl)-1,1,3,3-tetramethylaminium hexafluorophosphate (HBTU) and 6 eq DIPEA in DMF. Alternatively other basic coupling conditions might be used or even HOBt hydrate and DIC. Coupling mixture is added to the resin. Coupling proceeds for 3-4 hours.
i) Coupling mixture is removed from the resin. Resin is washed twice with DMF.

j) Fmoc-group is cleaved by 2 treatments with piperidine (20% in DMF) for and 20 minutes
k) Cleavage solution is washed from the resin and the resin is washed 6× with DMF
l) 3 to 3.5 eq of palmitic acid are activated with 3 to 3.5 eq hydroxybenzotriazol hydrate (HOBt Hydrate) and 3 to 3.5 eq of diisopropyl carbodiimide (DIC) for 10 minutes in DMF. Preactivated fatty acid is given to the resin. The coupling proceeds for 4-22 hours.

m) The coupling solution is removed from the resin. The resin is washed twice with DMF, 3 times with IPA and 3 times with DIPE and dried under vacuum.
n) Peptide on resin is now ready for cleavage to obtain crude peptide if test cleavage shows only minimal amount of SEQ ID NO: 2.

The following scheme shows the principal procedure for the Mmt-cleavage with subsequent couplings.

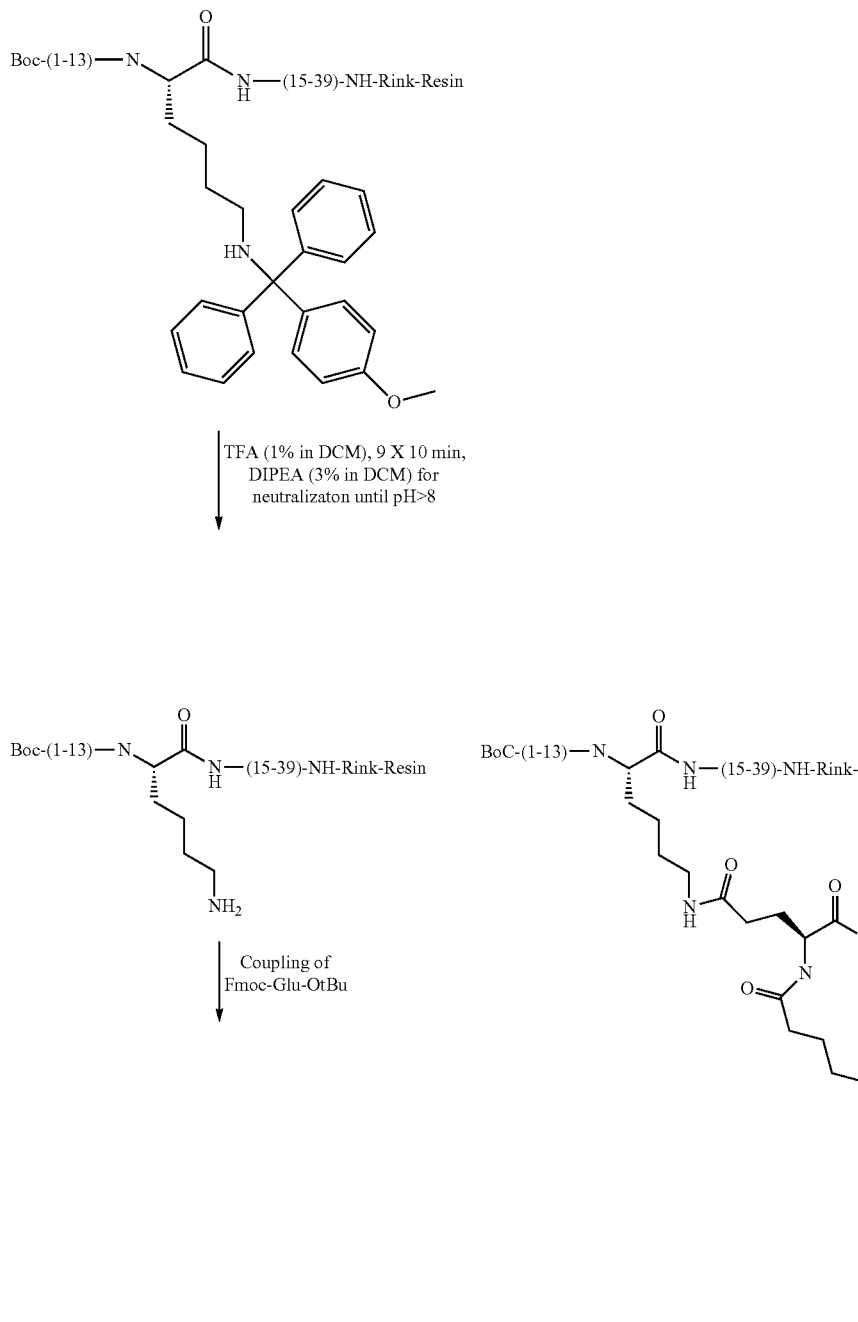

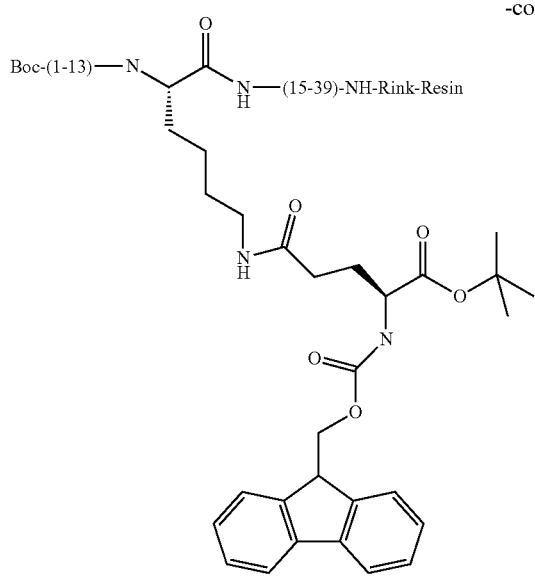
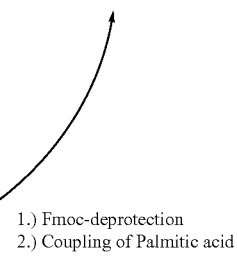

1.) Fmoc-deprotection
2.) Coupling of Palmitic acid

The following workflow shows the principal reprocessing procedure for the Mmt-cleavage with subsequent couplings.
  a) Dried resin is treated 5-9 times with TFA (1% in DCM) for 10 minutes each
  b) Washing of resin with DCM
  c) Several neutralization steps by treating resin with diisopropyl ethylamine (DIPEA, 3% in DCM) for 10 minutes each, pH-control of washing solution, end point: pH>8
  d) Washes with DCM (1×) and DMF (3×)
  e) Activation of 3 eq Fmoc-Glu-OtBu with 3 eq 2-(1H-Benzotriazole-1-yl)-1,1,3,3-tetramethylaminium hexafluorophosphate (HBTU) and 6 eq DIPEA in DMF. Alternatively other basic coupling conditions might be used or even HOBt hydrate and DIC. Coupling mixture is added to the resin. Coupling proceeds for 3-4 hours.
  f) Coupling mixture is removed from the resin. Resin is washed twice with DMF.
  g) Fmoc-group is cleaved by 2 treatments with piperidine (20% in DMF) for and 20 minutes
  h) Cleavage solution is washed from the resin and the resin is washed 6× with DMF
  i) 3 to 3.5 eq of palmitic acid are activated with 3 to 3.5 eq hydroxybenzotriazol hydrate (HOBt Hydrate) and 3 to 3.5 eq of diisopropyl carbodiimide (DIC) for 10 minutes in DMF. Preactivated fatty acid is given to the resin. The coupling proceeds for 4-22 hours.
  j) The coupling solution is removed from the resin. The resin is washed twice with DMF, 3 times with IPA and 3 times with DIPE and dried under vacuum.
  k) Peptide on resin is now ready for cleavage to obtain crude peptide.

The application of this novel Mmt-cleavage procedure, optionally together with a reprocessing procedure allows the access to a crude peptide with low amounts of undesired SEQ ID NO: 2.

In summary, the following key steps can be taken to achieve a high rate of modification of Lys(14): Start Mmt-cleavage with a pre-dried resin, perform the Mmt-cleavage with 1% TFA in DCM nine times, perform a neutralization step with pH-control, apply a reprocessing procedure for bigger scales if Mmt-cleavage was not complete.

Example 3: Cleavage of the Peptide from the Resin

After the solid-phase synthesis was finished, the peptide has to be cleaved from the resin and also the acid-labile side-chain protecting groups have to be removed. These concomitant reactions may be performed with King's cocktail which consists of 82.5% trifluoroacetic acid (TFA), 5% water, 2.5% 1,2-ethanedithiol (EDT), 5% thioanisole and 5% phenol (King et al., Int. J. Peptide Protein Res. 36, 255-266, 1990). The cleavage is performed at room temperature (20° C.) for 4 h. The conditions can be optimized for every peptide, also for SEQ ID NO: 1. However, it was surprisingly found that other cleavage cocktails provide better results, as set forth in detail below.

In a first set of experiments samples of peptide-on-resin were treated with different cleavage cocktails. For a 1 g-sample, 8.5 ml of TFA, 0.5 ml of water, 0.25 ml of EDT, 0.5 ml of thioanisole and 0.5 g of phenol were used as reference, cleavage time 4 h, room temperature. The resulting peptide was precipitated in diisopropyl ether and centrifuged. Diisopropyl ether was decanted. The obtained peptide pellet was shaken up with ethyl acetate and centrifuged again. After a further decantation this procedure was repeated 3 times. Finally the peptide was dried under vacuum. Analytics was performed on the sample: UV-purity (%) via HPLC, HPLC content (%), yield in g/g of peptide-on-resin (line 1 in table 3). In a stepwise manner an ingredient was omitted one after the other, then two and finally three. The next table (Table 3) shows the results.

TABLE 3

Comparison of different cleavage cocktails for the cleavage of SEQ ID NO: 1 from the resin

| phenol | water | thioanisole | ethanedithiol | HPLC-UV (%) | HPLC content (%) | Yield in g/g of resin |
|---|---|---|---|---|---|---|
| + | + | + | + | 65.1 | 37.1 | 0.16 |
| + | − | + | + | 63.3 | 35.2 | 0.16 |

TABLE 3-continued

Comparison of different cleavage cocktails for
the cleavage of SEQ ID NO: 1 from the resin

| | | | | | | |
|---|---|---|---|---|---|---|
| − | + | + | + | 64.9 | 36.4 | 0.16 |
| + | + | + | − | 62.2 | 34.8 | 0.15 |
| + | + | − | + | 70   | 41.1 | 0.18 |
| + | − | + | − | 59.7 | 28.8 | 0.14 |
| + | − | − | + | 70.1 | 38   | 0.19 |
| − | − | + | + | 62.6 | 33.2 | 0.16 |
| − | − | − | + | 70.1 | 38.1 | 0.18 |

+ used
− not used

The best results were obtained if thioanisole is omitted and if EDT is used. In a second group of experiments 3 cocktails were investigated over time at 20° C.: cocktail 1 consisting of TFA, phenol, EDT, water; cocktail 2 consisting of TFA, phenol, EDT; cocktail 3 consisting of TFA, EDT. In table 4 the results are depicted.

TABLE 4

Comparison of 3 cocktails over time at 20° C.

| | | 2 h | 3 h | 4 h | 5 h |
|---|---|---|---|---|---|
| Cocktail (1) | HPLC-UV (%) | 68.8 | 70.1 | 70 | 67.5 |
| | HPLC Content (%) | 40.7 | 40.8 | 41.1 | 32.2 |
| | Yield in g/g of resin | 0.17 | 0.18 | 0.18 | 0.15 |
| Cocktail (2) | HPLC-UV (%) | 71.9 | 71.6 | 70.1 | |
| | HPLC Content (%) | 41.5 | 38.9 | 38 | |
| | Yield in g/g of resin | 0.18 | 0.18 | 0.19 | |
| Cocktail (3) | HPLC-UV (%) | 72 | 71.1 | 69.7 | 68 |
| | HPLC Content (%) | 41.9 | 39.3 | 29.3 | 25.9 |
| | Yield in g/g of resin | 0.18 | 0.19 | 0.16 | 0.12 |

Results for the cocktails 2 and 3 are equally good. Four hours are not needed for the complete cleavage of the peptide from the resin. The experiments for cocktail 2 and 3 were repeated at 25° C. and the results in table 5 were obtained.

TABLE 5

Comparison of cocktail 2 and 3 at 25° C.

| | | 1.5 h | 2 h | 2.5 h | 3 h | 4 h |
|---|---|---|---|---|---|---|
| Cocktail (2) | HPLC-UV (%) | 68.1 | 67.6 | 66.3 | 65.5 | 63.1 |
| | HPLC Content (%) | 43.8 | 42.1 | 41.9 | 38.2 | 38 |
| | Yield in g/g of resin | 0.18 | 0.18 | 0.19 | 0.17 | 0.17 |
| Cocktail (3) | HPLC-UV (%) | 68 | 67.1 | 66.2 | 64.9 | 65 |
| | HPLC Content (%) | 43.1 | 42.3 | 41.7 | 37.8 | 35 |
| | Yield in g/g of resin | 0.18 | 0.19 | 0.19 | 0.18 | 0.15 |

Cleavage with cocktail 2 and 3 give comparable results. Cleavage time could be reduced to 2 h at 25° C.

Furthermore it was tested whether the volume of the cocktails could be reduced for 20% and 30%. Table 6 shows the results over time at 25° C.

TABLE 6

Reduction of volume of cleavage
cocktail 2 and 3 for 20% and 30%

| | | 1.5 h | 2 h | 2.5 h | 3 h | 4 h |
|---|---|---|---|---|---|---|
| Cocktail (2) −20% | HPLC-UV (%) | 67.8 | 67.1 | 65.6 | 66 | 63.1 |
| | HPLC Content (%) | 44.4 | 43.6 | 42 | 38.9 | 27.1 |
| | Yield in g/g of resin | 0.19 | 0.19 | 0.19 | 0.18 | 0.13 |
| Cocktail (2) −30% | HPLC-UV (%) | 67.4 | 66.9 | 66.6 | 65.6 | 63.5 |
| | HPLC Content (%) | 44.8 | 43.2 | 42.1 | 42.3 | 38.2 |
| | Yield in g/g of resin | 0.19 | 0.19 | 0.19 | 0.2 | 0.18 |
| Cocktail (3) −20% | HPLC-UV (%) | 67.9 | 67 | 66.4 | 65.2 | 63.5 |
| | HPLC Content (%) | 44.2 | 43.2 | 41.9 | 39.9 | 31.9 |
| | Yield in g/g of resin | 0.2 | 0.2 | 0.2 | 0.19 | 0.16 |
| Cocktail (3) −30% | HPLC-UV (%) | 67.9 | 66.7 | 65.6 | 64.7 | 63.1 |
| | HPLC Content (%) | 43.7 | 43.1 | 41.6 | 40.1 | 31.9 |
| | Yield in g/g of resin | 0.2 | 0.2 | 0.2 | 0.19 | 0.17 |

As can be seen in table 6, no significant differences are encountered. During reduction of volume of the cleavage cocktail of 70% stirring could be hardly maintained during cleavage reaction because of the viscosity of the slurry.

For confirmation, the cleavages with King's Cocktail, with cocktail 2 and 3 were repeated on a 10 g scale of peptide-on-resin. The volumes of the cleavage cocktails were reduced by distillation prior to precipitation of the peptide in diisopropyl ether.

King's Cocktail:

The cocktail was mixed by using 5 g of phenol, 5 ml of thioanisole, 2.6 ml of EDT, 79.2 ml of TFA and 5 ml of water. 10 g of peptide-on-resin were given to the precooled mixture (10-15° C.). The slurry was stirred for 4 h at 17-23° C. The resin was filtered off and washed 4 times with 10.1 ml of TFA each. The combined solutions were distilled at reduced pressure at a temperature of <30° C. to obtain a remaining volume of 60 ml. This solution was given to 276 ml of diisopropyl ether within 30-60 minutes at 0-5° C. The flask was washed with 3.4 ml of TFA which were also added to the diisopropyl ether. The obtained slurry was stirred for at least 10 h at 10-15° C. The precipitate was isolated by centrifugation. After decantation the pellet was suspended in 66.2 ml of ethyl acetate and centrifuged again. This procedure was repeated three more times. Finally, 4.20 g of crude peptide were obtained with a purity of 54.9% and a content of 33.4%.

Cocktail 2:

The cocktail was mixed by using 4 g of phenol, 2 ml of EDT and 68 ml of TFA. 10 g of peptide-on-resin were given to the precooled mixture (10° C.). The slurry was stirred for 2 h at 25° C. The resin was filtered off and washed 4 times with 8 ml of TFA each. The combined solutions were distilled at reduced pressure at a temperature of <30° C. to obtain a remaining volume of 35 ml. This solution was given to 276 ml of diisopropyl ether within 10 minutes at 3° C. The flask was washed with 3.4 ml of TFA which were also added to the diisopropyl ether. The obtained slurry was stirred for at least 1 h at 15° C. The precipitate was isolated by centrifugation. After decantation the pellet was suspended in 66.2 ml of ethyl acetate and centrifuged again. This procedure was repeated three more times. Finally 4.88 g of crude peptide were obtained with a purity of 64.2% and a content of 37.1%.

Cocktail 3:

The cocktail was mixed by using 2 ml of EDT and 68 ml of TFA. 10 g of peptide-on-resin were given to the precooled mixture (10° C.). The slurry was stirred for 2 h at 25° C. The resin was filtered off and washed 4 times with 8 ml of TFA each. The combined solutions were distilled at reduced pressure at a temperature of <30° C. to obtain a remaining volume of 37 ml. This solution was given to 276 ml of diisopropyl ether within 10 minutes at 3° C. The flask was washed with 3.4 ml of TFA which were also added to the diisopropyl ether. The obtained slurry was stirred for at least 1 h at 15° C. The precipitate was isolated by centrifugation. After decantation the pellet was suspended in 66.2 ml of ethyl acetate and centrifuged again. This procedure was repeated three more times. Finally 5.10 g of crude peptide were obtained with a purity of 64.2% and a content of 36.4%.

TABLE 7

Comparative results of cleavages with different cocktails at 10 g scale

| | HPLC-UV (%) | HPLC-content (%) | Yield (g) |
|---|---|---|---|
| King's cocktail | 54.9 | 33.4 | 4.20 |
| Cocktail (2) | 64.2 | 37.1 | 4.88 |
| Cocktail (3) | 64.2 | 36.4 | 5.10 |

It was found as depicted in table 7 that the application of cocktail 2 and 3 give far better results in terms of purity, content and yield compared to the application of King's cocktail.

Cocktail 3 was used to treat 7.6 kg of peptide-on-resin on production scale due to the fact that it gave the highest yield and HPLC-UV-purity (Table 7). In total 3.26 kg of SEQ ID NO:1 were obtained with a purity of 68.7%.

In summary, the following key steps can be taken: Instead of using the complex King's cocktail for the cleavage of the peptide from the resin only TFA and EDT is used, the cleavage is performed for 2 h at 25° C., the volume of cleavage cocktail/g of peptide-on-resin is reduced.

Example 4: Cleavage of the Peptide from the Resin

Further experiments were carried out to optimize cleavage of the peptide from the resin. A particular focus of these experiments was to keep the occurrence of an unwanted side product, which can form during the cleavage step between tryptophane moieties of the peptide and a degradation product from the Rink resin linker, at a tolerable minimum. In the following, this particular side product is also referred to as "SP1". The undesired side product apparently can form until the peptide of interest, e.g. SEQ ID NO.:1, is precipitated (step (xii)). For instance, when using King's cocktail for the cleavage, the side product can accumulate up to several percent, based on UV purity (HPLC) measurements.

Example 4.1: Variation in the Proportion of EDT

In a first set of experiments, samples of peptide-on-resin (SEQ ID NO.: 1) were treated with a cleavage cocktail consisting of TFA and EDT, where the EDT proportion was varied. Cleavage was performed for 2 hours at 25° C., and each sample was incubated at ambient temperature for further two hours. After two or four hours, samples were analyzed via HPLC.

TABLE 8

Variation of EDT proportion in the cleavage cocktail

| EDT proportion* | 0.0 | 1.0 | 2.0 | 3.1 | 6.2 | 9.3 |
|---|---|---|---|---|---|---|
| side product SP1**, 2 h | 0.9 | 1.2 | 1.6 | 1.3 | 1.3 | 1.2 |
| SEQ ID NO.: 1**, 2 h | 63.3 | 62.7 | 71.7 | 74.2 | 74.5 | 74.9 |

TABLE 8-continued

Variation of EDT proportion in the cleavage cocktail

| EDT proportion* | 0.0 | 1.0 | 2.0 | 3.1 | 6.2 | 9.3 |
|---|---|---|---|---|---|---|
| side product SP1**, 4 h | 1.3 | 2 | 3.3 | 3 | 2.8 | 2.6 |
| SEQ ID NO.: 1**, 4 h | 60.8 | 57.7 | 66.1 | 69.5 | 70.5 | 70.4 |

*in % (v/v) of the cleavage cocktail
**in % UV purity (HPLC)

As can be seen from Table 8, increasing the EDT proportion has only little influence on the formation of the side product (SP1).

Example 4.2: Addition of a Further Scavenger Compound

A similar set of experiments as in Example 4.1 was carried out, where the proportion of EDT was kept constant at 3.1% (v/v) of the cleavage cocktail, and either thioanisole or 3-methylindole was added as a further scavenger compound. Incubation and analysis via HPLC were as described in Example 4.1.

TABLE 9

Addition of thioanisole to the cleavage cocktail

| EDT proportion* | | | 3.1 | | | |
|---|---|---|---|---|---|---|
| thioanisole proportion* | | 2.5 | | 5.0 | | 7.5 |
| | side product SP1** | SEQ ID NO.: 1** | side product SP1** | SEQ ID NO.: 1** | side product SP1** | SEQ ID NO.: 1** |
| 2 hours | 1.6 | 66.5 | 1.5 | 65.1 | 1.3 | 63.6 |
| 4 hours | 2.6 | 64.4 | 2.4 | 63.2 | 2.2 | 63.0 |

*in % (v/v) of the cleavage cocktail
**in % UV purity (HPLC)

TABLE 10

Addition of 3-methylindole to the cleavage cocktail

| TFA proportion* | | 94.4 | | 91.9 | | 89.4 |
|---|---|---|---|---|---|---|
| EDT proportion* | | | 3.1 | | | |
| 3-methyl-indole proportion** | | 2.5 | | 5.0 | | 7.5 |
| | side product SP1*** | SEQ ID NO.: 1*** | side product SP1*** | SEQ ID NO.: 1*** | side product SP1*** | SEQ ID NO.: 1*** |
| 2 hours | 1.0 | 71.0 | 1.3 | 68.7 | 1.0 | 68.5 |
| 4 hours | 1.3 | 66.2 | 1.3 | 64.6 | 1.3 | 63.0 |

*in % (v/v) of the cleavage cocktail
**in % (v/v)( ) of the cleavage cocktail;
note:
3-methylindole is solid at the used temperature; thus, a hypothetical volume was calculated based on a density of 1.22 g/cm³ (known in the literature) to be able to give %(v/v) values
***in % UV purity (HPLC)

The (w/w) ratio of the above cleavage cocktail would be 95.57% (w/w) TFA, 2.36% (w/w) EDT and 2.07% (w/w) 3-MI. As can be seen from Tables 9 and 10, the addition of thioanisole had hardly any effect on the occurrence of the side product SP1, whereas by the addition of 3-methylindole, the side product could be kept at a low level, even after a total of four hours incubation time.

Example 4.3: Comparison of Indole Compounds

In a further set of experiments similar to Example 4.1, it was analyzed whether a further indole compound, N-acetylindole, shows a similar suppressive effect on the side product as compared to that of 3-methylindole. The proportion of EDT was kept constant at 3.1% (v/v) of the cleavage cocktail, and either no further compound (control), 3.1% (v/v) N-acetylindole (N-acetylindole is a viscous liquid) or 3.1% (v/v) 3-methylindole (calculation % (v/v) as described in the note in Table 10) was added. Incubation and analysis via HPLC were as described in Example 4.1.

TABLE 11

Comparison of N-acetylindole and 3-methy indole in cleavage cocktail

| cleavage cocktail | side product SP1 (% UV purity (HPLC)) | SEQ ID NO.: 1 (% UV purity (HPLC)) |
|---|---|---|
| TFA/EDT/3-methylindole | | |
| 2 hours | 0.9 | 72.6 |
| 4 hours | 1.6 | 66.7 |
| TFA/EDT/N-acetylindole | | |
| 2 hours | 0.9 | 70 |
| 4 hours | 1.4 | 62.4 |
| TEA/EDT (control) | | |
| 2 hours | 1.3 | 74.2 |
| 4 hours | 3 | 69.5 |

As shown in Table 11, both 3-methylindole and N-acetylindole are effective in reducing the formation of undesired side product SP1.

Example 4.4: Variation of Proportion of 3-Methylindole

In a further set of experiments similar to Example 4.1, the amount of 3-methylindole added to the cleavage cocktail was varied to determine the most suitable concentrations. The proportion of EDT was kept constant at 3.1% (v/v) of the cleavage cocktail. Incubation and analysis via HPLC were as described in Example 4.1.

TABLE 12

Variation of 3-methylindole proportion

| 3-methylindole proportion* | side product SP1 (% UV purity (HPLC)) | SEQ ID NO.: 1 (% UV purity (HPLC)) |
|---|---|---|
| 0.8% (v/v) 3-methylindole | | |
| 2 hours | 1 | 72 |
| 4 hours | 1.4 | 68 |
| 1.7% (v/v) 3-methylindole | | |
| 2 hours | 0.9 | 71.1 |
| 4 hours | 1.3 | 66.6 |
| 2.5% (v/v) 3-methylindole | | |
| 2 hours | 1 | 70.2 |
| 4 hours | 1.3 | 65.5 |
| 5.0% (v/v) 3-methylindole | | |
| 2 hours | 1.3 | 68.7 |
| 4 hours | 1.3 | 64.6 |
| 7.5% (v/v) 3-methylindole | | |
| 2 hours | 1.0 | 68.5 |
| 4 hours | 1.3 | 63.0 |

*calculation % (v/v) as described in note to Table 10

As can be seen from Table 12, an amount of 0.8% (v/v) 3-methylindole is already sufficient to suppress formation of intolerable amounts of the side product.

Taken together, the inventors have surprisingly found a possibility to reduce occurrence of an undesired side product to a tolerable amount. By adding a suitable indole compound, in particular N-acetylindole or 3-methylindole, the amount of undesired side product could be reduced to only 1.0 to 1.3% UV purity (HPLC) in the crude desired product. The indole compound, e.g. 3-methylindole, as well as adducts of scavenger molecules and protective groups are removed from the desired peptide especially during washing of the precipitated peptide solution.

Example 5: Test Cleavage of SEQ ID NO.: 1 from Resin (Kilogram Scale)

6.5-7.5 kg of resin-bound peptide is treated with a mixture of 76.13 kg of trifluoroacetic acid (TFA), 1.8 kg of 1,2-ethanedithiol and 0.656 kg of 3-methylindole for 2-2.5 h at 25° C. The resin is filtered off and washed 3 times with 17.5 kg TFA each. The combined TFA phases are evaporated to ⅓ of its original volume. The distillation residue is given onto 203 L of a mixture of diisopropyl ether and n-heptane (30:70 (v/v)) at 0-5° C. for precipitation of the peptide. The suspension is stirred for 10-20 h at 10-15° C. followed by separation of the peptide by filtration. The resulting filter cake is washed 5 times with 50 L of ethyl acetate each. Finally the peptide on the filter is dried under vacuum and 2.5-3.2 kg of crude peptide is obtained.

In a specific experiment, 7.24 kg of SEQ ID NO.:1 on resin were subjected to cleavage and further washing and isolation steps as listed below, and 2.55 kg dry crude peptide were obtained. The product was a white to slightly yellowish powder, with a HPLC-purity of 68.2% and a content of the undesired degradation product of the Rink linker and tryptophane residue of the peptide of 1.2%: To achieve these results, 7.24 kg of SEQ ID NO.: 1 were treated with a mixture of 73.2 kg TFA, 1.73 kg of 1,2-ethanedithiol and 0.63 kg of 3-methylindole for 2.15 h at 23-25° C. The resin was filtered off then and washed 3 times with 17.4 kg of TFA each. The combined TFA phases (cleavage mixture and TFA-washes) were transferred to distillation. Distillation was performed at ≤50 mbar and ≤30° C. temperature until 29 L volume was obtained within 1 h. The remainder was given to a mixture of 60.9 L of DIPE and 142.1 L of n-heptane at 0-5° C. within 35 minutes, a suspension was obtained. The suspension was stirred at 10-15° C. for about 17 h. The crude peptide was filtered off within 2.5 h followed by 5 washes of the crude peptide with 49.4 L of ethyl acetate each (addition of ethyl acetate, 30-60 minutes stirring, removal of solvent). The wet peptide was dried for >96 h at 20-25° C. under vacuum (<100 mbar) with stripping nitrogen. Finally 2.55 kg of crude peptide were obtained.

Example 6: Effect of Concentrating Peptide Solution after Cleavage on Filtration Time In a small batch experiment using 10 grams of resin each, a peptide of interest (SEQ ID NO.: 1) was synthesized via SPPS as described herein and cleaved from the resin using 67.8 ml of TFA and 2.26 ml of EDT at 25° C. for 2 h.

The peptide solution was filtered to remove the resin and then either concentrated by vacuum distillation at ≤80 mbar and ≤30° C. to about one third of its volume before being precipitated or directly precipitated (without concentration). Diisopropyl ether was used as antisolvent. The precipitate was washed three times with ethyl acetate. The time required for filtration after the precipitation and after each of the ethyl acetate washes was recorded.

TABLE 13

Filtration times in DIPE with and without prior concentration of peptide solution

| antisolvent | concentration of peptide prior to precipitation | precipitation step | time (in min) required for filtration after | | |
|---|---|---|---|---|---|
| | | | 1st wash with ethyl acetate | 2nd wash with ethyl acetate | 3rd wash with ethyl acetate |
| DIPE | yes | 65 | 35 | 45 | 55 |
| DIPE | no | 200 | 60 | 70 | n.d. | n.d = not determined

It can be seen that when the concentration step is performed, the time required for filtration, particularly after the initial precipitation, can be strongly reduced.

Example 7: Precipitation of Crude Peptide in Mixtures of DIPE and n-Heptane

The present inventors surprisingly found that mixtures of diisopropyl ether (DIPE) and n-heptane can strongly reduce the time required for filtration and subsequent washing with ethyl acetate.

To optimize the ratio of DIPE and n-heptane, small batch experiments using 10 grams of resin were performed. The peptide was synthesized via SPPS as described herein and cleaved from the resin using 67.2 ml of TFA, 2.1 ml of EDT and 0.86 g of 3-MI at 25° C. for 2 h.

The peptide solution was then filtered to remove the resin and concentrated by vacuum distillation at ≤80 mbar and ≤30° C. to about one third of its volume. Subsequently, the concentrated peptide solution was precipitated either with DIPE alone or with mixtures of DIPE and n-heptane and filtered. The precipitate was washed three times with ethyl acetate. The time required for filtration after the precipitation and after each of the ethyl acetate washes was recorded.

TABLE 14

Filtration times in DIPE and DIPE/n-heptane mixtures

| antisolvent | ratio DIPE:n-heptane (v/v) | precipitation step | time (in min) required for filtration after | | |
|---|---|---|---|---|---|
| | | | 1st wash with ethyl acetate | 2nd wash with ethyl acetate | 3rd wash with ethyl acetate |
| DIPE | n/a | 95 | 30 | — | 65 |
| DIPE/n-heptane | 20:80 | 0.3 | 3.2 | 3.8 | 5.1 |
| DIPE/n-heptane | 25:75 | 1.1 | 1.3 | 3.8 | 2.5 |
| DIPE/n-heptane | 30:70 | 1.5 | 2.7 | 4.5 | 5.3 |
| DIPE/n-heptane | 35:65 | 5.3 | 5.7 | 7.5 | 12.5 |
| DIPE/n-heptane | 40:60 | 7.7 | 7.2 | 10.7 | 14.5 | n/a = not applicable

As demonstrated by the results in Table 14, the filtration time decreases with increasing amounts of n-heptane in the mixture. However, at ratios of DIPE:n-heptane above 25:75, it was observed that the peptide "melts" on the filtration frit. At ratios of DIPE:n-heptane below 40:60, the time reduction effect is less pronounced.

Further analysis of the samples by HPLC showed that after the third wash with ethyl acetate, no scavenger compounds or adducts of scavengers and protecting groups were detectable any more.

Example 8: Test Purification of Crude Peptide Using DIPE/n-Heptane as Antisolvent (Laboratory Scale)

20 g peptide on resin (peptide: SEQ ID NO.:1) were cleaved by incubation with cleavage cocktail (198.8 g TFA, 4.7 g EDT, 1.72 g 3-MI) for 3 hours at 25° C. The cleaved peptide was aspirated through a frit and the resin remaining on the frit was washed four times with 16 ml each TFA.

The filtrate was concentrated in a rotary evaporator at 30° C. and the remaining solution was added to 560 ml DIPE/n-heptane (30:70), which was precooled to 5-10° C. The peptide precipitated and was steered for one hour at 8° C. The suspension was then aspirated over a D4-frit, which required 3.6 minutes. The crude product was suspended in 520 ml ethyl acetate, stirred and aspirated through the same D4 frit. This washing step was repeated two more times. Subsequently, the crude product was dried under vacuum. This yielded 8.36 g crude product with a purity of 66.6%.

The invention is further characterized by the following items.

1. A method of preparing an isolated peptide comprising a lipophilically modified lysine side chain, comprising the steps of:
(i) assembling the amino acid sequence of said peptide with protected reactive functional groups in the side chains in a step-wise manner using solid phase peptide synthesis (SPPS), wherein the side chain of lysine to be modified is protected by a trityl-based protecting group, particularly monomethoxytrityl (Mmt) or 4-methyltrityl (Mtt);
(ii) drying the solid phase resin after the assembling of the amino acid sequence has been completed;
(iii) treating the dried resin several times with a solution of trifluoroacetic acid (TFA) in dichloromethane (DCM) in order to deprotect the lysine side chain to be modified;
(iv) neutralizing the resin;
(v) coupling at least one activated 9-fluorenylmethyloxycarbonyl (Fmoc)-bound linker moiety to the deprotected lysine side chain;
(vi) deprotecting the terminal functional group of the linker coupled to the lysine side chain in step (v);
(vii) coupling an activated lipophilic moiety, particularly an activated fatty acid, to the deprotected terminal functional group of the linker of step (vi);
(viii) drying the resin; and
(ix) cleaving the peptide from the resin.

2. The method of item 1, wherein the isolated peptide is an exendin-4 derivative having a length of between 30 and 44 amino acids, and wherein the sequence identity to wild-type exendin-4 in the region corresponding to amino acids 1-13 of wild-type exendin is at least 65%.

3. The method of item 1 or 2, wherein the isolated peptide is an exendin-4 derivative having a length of between 30 and 44 amino acids, and wherein the sequence identity to wild-type exendin-4 in the region corresponding to amino acids 22-39 of wild-type exendin is at least 70%.

4. The method of any one of items 1-3, wherein the isolated peptide is an exendin-4 derivative having a length of between 30 and 44 amino acids, and wherein the lipophilically modified lysine side chain is at position 14 (Lys(14)) with respect to the amino acid positions of wild-type exendin-4.

5. The method of any one of the preceding items, wherein the isolated peptide is an exendin-4 derivative having a length of between 30 and 44 amino acids, wherein the sequence identity to wild-type exendin-4 in the region corresponding to amino acids 1-13 of wild-type exendin is at least 65%, the sequence identity to wild-type exendin-4 in the region corresponding to amino acids 22-39 of wild-type exendin is at least 70%, and wherein the lipophilically modified lysine side chain is at position 14 (Lys(14)) with respect to the amino acid positions of wild-type exendin-4.

6. The method of any one of the preceding items, wherein the isolated peptide is an exendin-4 derivative having a length of between 38 and 40 amino acids.

7. The method of any one of the preceding items, wherein the isolated peptide is an exendin-4 derivative having a length of 39 amino acids.

8. The method of any one of the preceding items, wherein the isolated peptide is an exendin-4 derivative having a length of 39 amino acids, wherein the sequence in the region corresponding to amino acids 1-13 of wt exendin-4 contains no more than 2 mutations, the region corresponding to amino acids 22-39 of wt exendin-4 contains no more than one mutation, and wherein the lipophilically modified lysine side chain is at position 14 (Lys(14)) with respect to the amino acid positions of wt exendin-4.

9. The method of any one of the preceding items, wherein the isolated peptide is an exendin-4 derivative having a length of 39 amino acids, wherein the region corresponding to amino acids 1-13 of wt exendin-4 contains mutations in positions 2 and 3, the region corresponding to amino acids 22-39 of wt exendin-4 contains a mutation in position 28, and wherein the lipophilically modified lysine side chain is at position 14 (Lys(14)) with respect to the amino acid positions of wt exendin-4.

10. The method of any one of the preceding items, wherein the number of TFA in DCM treatments in step (iii) is adjusted such that the yield of modified lysine side chain in step (ix) is at least 85%, or at least 90%, or at least 95%.

11. The method of any one of the preceding items, wherein, in step (iii), the dried resin is treated at least seven times for at least 5 minutes with a solution of about 1% (v/v) TFA in DCM.

12. The method of any one of the preceding items, wherein, in step (iii), the dried resin is treated nine times for at least 10 minutes with a solution of about 1% (v/v) TFA in DCM.

13. The method of any one of the preceding items, wherein, in step (iii), the dried resin is treated nine times for at least 15 minutes with a solution of about 1% (v/v) TFA in DCM.

14. The method of any one of the preceding items, wherein, in step (iv), the peptide is considered sufficiently neutralized once a pH of ≥7, particularly ≥7.5, more particularly ≥8.0 is reached.

15. The method of any one of the preceding items, wherein, in step (iv), the peptide is considered sufficiently neutralized once >8.0 is reached.

16. The method of any one of the preceding items, further comprising the step of: (viii-a) analyzing the deprotection yield of step (iii) by cleaving a test sample of the resin bound peptide.

17. The method of any one of the preceding items, further comprising the step of: (viii-b) repeating steps (iii) to (viii-a) until the content of cleaved peptide containing the modified lysine side chain is at least 85%, particularly at least 90%, more particularly at least 95% compared to peptide without modified lysine side chain.

18. The method of item 16, wherein analyzing the deprotection yield of step (iii) in a test sample comprises the steps of:

(viii-a1) removing a test sample of the resin from the total reaction batch and cleaving the peptide from the test sample under the same conditions and with the same cleavage cocktail as in step (ix); and (viii-a2) determining the content of cleaved peptide containing the modified lysine side chain in comparison to the peptide without modified lysine side chain, in particular by high pressure liquid chromatography (HPLC) or a combination of high pressure liquid chromatography and mass spectrometry (LC-MS).

19. The method of any one of the preceding items, wherein the isolated peptide has the amino acid sequence H-dS-Q-G-T-F-T-S-D-L-S-K-Q-K(γE-Palm)-E-S-K-A-A-Q-D-F-I-E-W-L-K-A-G-G-P-S-S-G-A-P-P-P-S-NH$_2$ (SEQ ID NO.: 1).

20. The method of any one of the preceding items, wherein the cleavage of step (ix) is performed with a cleavage cocktail comprising at least 90% (v/v) trifluoroacetic acid and at least 1% (v/v) ethanedithiol, which is free of thioanisole and ethylmethylsulfide.

21. The method of item 20, wherein the cleavage cocktail further comprises a suitable indole compound, e.g. N-acetylindole or 3-methylindole or mixtures thereof.

22. The method of item 21, wherein the suitable indole compound is 3-methylindole.

23. The method of item 20, wherein the cleavage cocktail consists of 91-93% (v/v) trifluoroacetic acid, 1-6% (v/v) phenol and 1-8% (v/v) ethanedithiol or consists of 96-98% (v/v) trifluoroacetic acid and 2-4% (v/v) ethanedithiol.

24. The method of any one of items 1-19, wherein the cleavage of step (ix) is performed with a cleavage cocktail comprising at least 80% (w/w) trifluoroacetic acid and at least 1% (w/w) 1,2-ethanedithiol, which is free of thioanisole and ethylmethylsulfide.

25. The method of item 24, wherein the cleavage cocktail further comprises a suitable indole compound, e.g. N-acetylindole or 3-methylindole or mixtures thereof.

26. The method of item 25, wherein the suitable indole compound is 3-methylindole.

27. The method of any one of items 24-26, wherein the cleavage cocktail consists of 88.2-98.3% (w/w) trifluoroacetic acid (TFA), 1-4.3% (w/w) 1,2-ethanedithiol (EDT) and 0.7-7.5% (w/w) 3-methylindole (3-MI).

28. The method of any one of items 24-27, wherein the cleavage cocktail consists of 96.0-97.5% (w/w) TFA, 1.7-2.6% (w/w) EDT and 0.7-1.5% (w/w) 3-MI.

29. The method of any one of items 24-28, wherein the cleavage cocktail consists of about 97% (w/w) TFA, about 2% (w/w) EDT and about 1% (w/w) 3-MI.

30. The method of any one of items 24-29, wherein the cleavage cocktail consists of about 96.9% (w/w) TFA, about 2.3% (w/w) EDT and about 0.8% (w/w) 3-MI.

31. The method of any one of items 20-30, wherein the cleavage is performed at 5-15° C., 15-22° C. and/or 22-30° C., particularly at 25° C.

32. The method of any one of items 20-31, wherein the volume of the cleavage cocktail per gram of peptide on resin is from 9.5 ml to 5.5 ml, particularly from 7.0 ml to 6.0 ml.

33. The method of any one of items 20-32, wherein the cleavage is performed for 2-3 hours, particularly 2.0-2.5 hours, with stirring.

34. The method of any one of items 20-33, wherein the cleavage is performed for 2-3 hours, particularly 2.0-2.5 hours, at 25° C. with stirring.

35. The method of any one of items 20-33, wherein the cleavage is performed for 1-1.5 hours at 30° C. with stirring.

36. The method of any one of items 20-35, wherein the cleavage is performed using (a) a cleavage cocktail consisting of 88.2-98.3% (w/w) trifluoroacetic acid, 1-4.3% (w/w) 1,2-ethanedithiol and 0.7-7.5% (w/w) 3-methylindole, particularly consisting of 96.0-97.5% (w/w) TFA, 1.7-2.6% (w/w) EDT and 0.7-1.5% (w/w) 3-MI, e.g. about 97% (w/w) TFA, about 2% (w/w) EDT and about 1% 3-MI, (b) an incubation time of only 2 hours at an elevated temperature of 25° C., and (c) a reduced volume of cleavage cocktail per gram peptide-on-resin, e.g. between 7.0 ml and 6.0 ml.

37. The method of any one of items 20-36, wherein the cleavage is performed using (a) a cleavage cocktail consisting of 88.2-98.3% (w/w) trifluoroacetic acid, 1-4.3% (w/w) 1,2-ethanedithiol and 0.7-7.5% (w/w) 3-methylindole, particularly consisting of 96.0-97.5% (w/w) TFA, 1.7-2.6% (w/w) EDT and 0.7-1.5% (w/w) 3-MI, e.g. about 97% (w/w) TFA, about 2% (w/w) EDT and about 1% 3-MI, (b) an incubation time of only 2 hours at an elevated temperature of 25° C., and (c) a reduced volume of cleavage cocktail per gram peptide-on-resin, e.g. between 7.0 ml and 6.0 ml, and wherein the peptide has the amino acid sequence of SEQ ID NO.: 1.

38. The method of any one of the preceding items, wherein drying of the resin in step (ii) is performed under inert gas, e.g. nitrogen at room temperature, subsequent to washing the peptide on resin at least once with an aliphatic alcohol and at least once with a dialkyl ether.

39. The method of item 38, wherein the aliphatic alcohol is isopropanol and the dialkyl ether is diisopropyl ether.

40. The method of any one of the preceding items, wherein neutralizing in step (iv) is performed by at least one incubation with a 1%-5% solution of a tertiary alkylamine in an organic polar aprotic solvent, for at least 10 minutes, optionally followed by determination of the pH of the solvent mixture after the neutralization step, and washing the peptide on resin at least once with said solvent and at least once with a further polar aprotic solvent, e.g. dimethylformamide (DMF).

41. The method of item 40, wherein the tertiary alkylamine is diisopropyl ethylamine (DIPEA) or N-methylmorpholine (NMM) or triethylamine, and wherein the organic polar aprotic solvent is dichloromethane.

42. The method of item 40 or 41, followed by determination of the pH of the solvent mixture after the neutralization step, and washing the peptide on resin at least once with said solvent and at least once with a further polar aprotic solvent, e.g. dimethylformamide (DMF).

43. The method of any one of the preceding items, wherein deprotecting in step (vi) is performed by treating the peptide on resin at least once for at least 5 minutes with a base, followed by at least one washing step.

44. The method of item 43, wherein the base is 20% (v/v) piperidine in DMF.

45. The method of any one of the preceding items, wherein drying of the resin in step (viii) is performed under vacuum, in particular under vacuum of ≤70 mbar, subsequent to washing the peptide on resin.

46. The method of any one of the preceding items, comprising the steps of:
(i) assembling the amino acid sequence of a peptide of SEQ ID NO.: 1 with protected reactive functional groups in the side chains in a step-wise manner using solid phase peptide synthesis (SPPS), wherein the side chain of lysine 14 is protected by monomethoxytrityl (Mmt);
(ii) drying the solid phase resin for at least 5 hours at room temperature after the assembling of the amino acid sequence has been completed;
(iii) treating the dried resin nine times for 10 minutes each with a solution of 1% (v/v) trifluoroacetic acid (TFA) in dichloromethane (DCM) in order to deprotect the lysine side chain at position 14;
(iv) neutralizing the resin with a solution of 3% diisopropyl ethylamine (DIPEA) in DCM, until the pH of the solution remains at ≥8;
(v) coupling an activated Fmoc-Glu-OtBu linker moiety to the deprotected lysine side chain under basic conditions;
(vi) cleaving the Fmoc group of the linker coupled to the lysine side chain in step (v) with 20% (v/v) piperidine in DMF;
(vii) coupling activated palmitic acid to the deprotected terminal functional group of the linker of step (vi);
(viii) drying the resin;
(viii-a) analyzing the deprotection yield of step (iii) by cleaving a test sample of the resin bound peptide; and
(viii-b) repeating steps (iii) to (viii-a) until the content of cleaved peptide containing the modified lysine side chain is at least 85%;
(ix) cleaving the peptide from the resin at 25° C. using a cleavage cocktail comprising at least 90% (v/v) trifluoroacetic acid and at least 1% (v/v) 1,2-ethanedithiol, which is free of thioanisole and ethylmethylsulfide.

47. The method of any one of the preceding items, further comprising the steps of:
(x) filtering the peptide solution after cleavage;
(xi) distilling the filtered peptide solution under vacuum;
(xii) adding the residual fraction from the distillation to an antisolvent comprising a dialkyl ether and a heptane;
(xiii) stirring the precipitated solution
(xiv) filtering the precipitated solution;
(xv) washing the precipitate; and
(xvi) drying the wet peptide.

48. The method of any one of the preceding items, wherein subsequent to step (x), the filter cake is rinsed at least once, e.g. 3 times, with a suitable rinsing solution, e.g. TFA.

49. The method of any one of the preceding items, wherein in step (xi) the distillation is performed at a vacuum of ≤50 mbar at a temperature of ≤30° C.

50. The method of any one of the preceding items, wherein in step (xii), the antisolvent is a mixture consisting of diisopropyl ether (DIPE) and n-heptane, particularly a mixture of DIPE and n-heptane in a ratio of from 25:75 (v/v) to 35:65 (v/v).

51. The method of item 50, wherein the ratio between DIPE and n-heptane is 30:70 (v/v).

52. The method of any one of the preceding items, wherein in step (xiii), the precipitated solution is stirred for 1-20 hours at 10-15° C.

53. The method of any one of the preceding items, wherein in step (xv), the precipitate on the filter is, subsequent to rinsing with a suitable organic solvent, e.g. ethyl acetate, washed at least once by resuspending the precipitate in a suitable organic solvent, e.g. ethyl acetate, stirring the resulting suspension, e.g. for 30-60 minutes, and filtering off the organic solvent.

54. The method of item 53, wherein the precipitate is washed 1-5 times, particularly 2-4 times or 3-5 times or 4-5 times with ethyl acetate.

55. The method of any one of the preceding items, wherein in step (xvi), the wet peptide is dried under vacuum, e.g. at 20-25° C., in particular under vacuum of ≤70 mbar at 20-25° C. and a nitrogen stream (stripping nitrogen).

56. The method of any one of the preceding items, comprising the steps of:

(i) assembling the amino acid sequence of a peptide of SEQ ID NO.: 1 with protected reactive functional groups in the side chains in a step-wise manner using solid phase peptide synthesis (SPPS), wherein the side chain of lysine 14 is protected by monomethoxytrityl (Mmt);
(ii) drying the solid phase resin for at least 5 hours at room temperature after the assembling of the amino acid sequence has been completed;
(iii) treating the dried resin nine times for 10 minutes each with a solution of 1% (v/v) trifluoroacetic acid (TFA) in dichloromethane (DCM) in order to deprotect the lysine side chain at position 14;
(iv) neutralizing the resin with a solution of 3% diisopropyl ethylamine (DIPEA) in DCM, until the pH of the solution remains at ≥8;
(v) coupling an activated Fmoc-Glu-OtBu linker moiety to the deprotected lysine side chain under basic conditions;
(vi) cleaving the Fmoc group of the linker coupled to the lysine side chain in step (v) with 20% piperidine in DMF;
(vii) coupling activated palmitic acid to the deprotected terminal functional group of the linker of step (vi);
(viii) drying the resin;
(viii-a) analyzing the deprotection yield of step (iii) by cleaving a test sample of the resin bound peptide;
(viii-b) repeating steps (iii) to (viii-a) until the content of cleaved peptide containing the modified lysine side chain is at least 85%;
(ix) cleaving the peptide from the resin using a cleavage cocktail consisting of 96.0-97.5% (w/w) TFA, 1.7-2.6% (w/w) EDT and 0.7-1.5% (w/w) 3-methylindole;
(x) filtering the peptide solution after cleavage at room temperature;
(xi) distilling the filtered peptide solution under vacuum at ≤30° C.;
(xii) adding the residual fraction from the distillation to an antisolvent consisting of DIPE and n-heptane in a ration of from 25:75 to 35:65;
(xiii) stirring the precipitated solution at 10-15° C. for 1-18 hours;
(xiv) filtering the precipitated solution;
(xv) washing the precipitate 4-5 times by (xv-a) resuspending the precipitate in ethyl acetate, (xv-b) stirring the resulting suspension for 30-60 minutes and (xv-c) filtering off ethyl acetate; and
(xvi) drying the wet peptide under vacuum.

The invention claimed is:

1. A method of preparing an isolated exendin-4 derivative peptide comprising a lipophilically modified lysine side chain, comprising the steps of:
   (i) assembling the amino acid sequence of said peptide with protected reactive functional groups in the side chains in a step-wise manner using solid phase peptide synthesis (SPPS), wherein the side chain of lysine to be modified is protected by a trityl-based protecting group;
   (ii) drying the solid phase resin after the assembling of the amino acid sequence has been completed;
   (iii) treating the dried resin several times with a solution of trifluoroacetic acid (TFA) in dichloromethane (DCM) in order to deprotect the lysine side chain to be modified;
   (iv) neutralizing the resin;
   (v) coupling at least one activated 9-fluorenylmethyloxycarbonyl (Fmoc)-bound linker moiety to the deprotected lysine side chain;
   (vi) deprotecting the terminal functional group of the linker coupled to the lysine side chain in step (v);
   (vii) coupling an activated lipophilic moiety to the deprotected terminal functional group of the linker of step (vi);
   (viii) drying the resin; and
   (ix) cleaving the peptide from the resin,
   thereby preparing the isolated exendin-4 derivative peptide comprising a lipophilically modified lysine side chain.

2. The method of claim 1, wherein the trityl-based protecting group is monomethoxytrityl (Mmt) or 4-methyltrityl (Mtt).

3. The method of claim 1, wherein the activated lipophilic moiety is an activated fatty acid.

4. The method of claim 1, wherein the exendin-4 derivative has a length of between 30 and 44 amino acids, wherein
   (i) the sequence identity to wild-type exendin-4 in the region corresponding to amino acids 1-13 of wild-type exendin is at least 65%, or
   (ii) the sequence identity to wild-type exendin-4 in the region corresponding to amino acids 22-39 of wild-type exendin is at least 70%, or
   (iii) the lipophilically modified lysine side chain is at position 14 (Lys(14)) with respect to the amino acid positions of wild-type exendin-4.

5. The method of claim 4, wherein the exendin-4 derivative has a length between 38 and 40 amino acids.

6. The method of claim 1, wherein, in step (iii), the dried resin is treated at least seven times for at least 5 minutes, with a solution of about 1% (v/v) TFA in DCM.

7. The method of claim 1, further comprising the steps of:
   (viii-a) analyzing the deprotection yield of step (iii) by cleaving a test sample of the resin bound peptide; and
   (viii-b) optionally repeating steps (iii) to (viii-a) until the content of cleaved peptide containing the modified lysine side chain is at least 85% compared to peptide without modified lysine side chain.

8. The method of claim 7, wherein the content of cleaved peptide containing the modified lysine side chain is at least 90% compared to peptide without modified lysine side chain.

9. The method of claim 7, wherein the content of cleaved peptide containing the modified lysine side chain is at least 95% compared to peptide without modified lysine side chain.

10. The method of claim 1, wherein the isolated peptide has the amino acid sequence H-dS-Q-G-T-F-T-S-D-L-S-K-Q-K(γE-Palm)-E-S-K-A-A-Q-D-F-I-E-W-L-K-A-G-G-P-S-S-G-A-P-P-P-S-$NH_2$ (SEQ ID NO.: 1).

11. The method of claim 1, wherein the cleavage of step (ix) is performed with a cleavage cocktail comprising at least 90% (v/v) trifluoroacetic acid and at least 1% (v/v) ethanedithiol, which is free of thioanisole and ethylmethylsulfide.

12. The method of claim 11, wherein the cleavage cocktail further comprises a suitable indole compound.

13. The method of claim 12, wherein the suitable indole compound is 3-methylindole.

14. The method of claim 1, wherein the cleavage of step (ix) is performed with a cleavage cocktail comprising at least 80% (w/w) trifluoroacetic acid and at least 1% (w/w) 1,2-ethanedithiol, which is free of thioanisole and ethylmethylsulfide.

15. The method of claim 14, wherein the cleavage cocktail consists of 88.2-98.3% (w/w) trifluoroacetic acid, 1-4.3% (w/w) 1,2-ethanedithiol and 0.7-7.5% (w/w) 3-methylindole.

16. The method of claim 1, further comprising the steps of:
   (x) filtering the peptide solution after cleavage;
   (xi) distilling the filtered peptide solution under vacuum;
   (xii) adding the residual fraction from the distillation to an antisolvent comprising a dialkyl ether and a heptane;
   (xiii) stirring the precipitated solution
   (xiv) filtering the precipitated solution;
   (xv) washing the precipitate; and
   (xvi) drying the wet peptide.

17. The method of claim 16, wherein in step (xii), the antisolvent is a mixture consisting of diisopropyl ether (DIPE) and n-heptane.

18. The method of claim 1, comprising the steps of:
   (i) assembling the amino acid sequence of a peptide of SEQ ID NO.: 1 with protected reactive functional groups in the side chains in a step-wise manner using solid phase peptide synthesis (SPPS), wherein the side chain of lysine 14 is protected by monomethoxytrityl (Mmt);
   (ii) drying the solid phase resin for at least 5 hours at room temperature after the assembling of the amino acid sequence has been completed;
   (iii) treating the dried resin nine times for 10 minutes each with a solution of 1% (v/v) trifluoroacetic acid (TFA) in dichloromethane (DCM) in order to deprotect the lysine side chain at position 14;

(iv) neutralizing the resin with a solution of 3% diisopropyl ethylamine (DIPEA) in DCM, until the pH of the solution remains at ≥8;
(v) coupling an activated Fmoc-Glu-OtBu linker moiety to the deprotected lysine side chain under basic conditions;
(vi) cleaving the Fmoc group of the linker coupled to the lysine side chain in step (v) with 20% (v/v) piperidine in DMF;
(vii) coupling activated palmitic acid to the deprotected terminal functional group of the linker of step (vi);
(viii) drying the resin;
(viii-a) analyzing the deprotection yield of step (iii) by cleaving a test sample of the resin bound peptide;
(viii-b) repeating steps (iii) to (viii-a) until the content of cleaved peptide containing the modified lysine side chain is at least 85%; and
(ix) cleaving the peptide from the resin at 25° C. using a cleavage cocktail comprising at least 90% (v/v) trifluoroacetic acid and at least 1% (v/v) ethanedithiol, which is free of thioanisole and ethylmethyl sulfide.

19. The method of claim 1, comprising the steps of:
(i) assembling the amino acid sequence of a peptide of SEQ ID NO.: 1 with protected reactive functional groups in the side chains in a step-wise manner using solid phase peptide synthesis (SPPS), wherein the side chain of lysine 14 is protected by monomethoxytrityl (Mmt);
(ii) drying the solid phase resin for at least 5 hours at room temperature after the assembling of the amino acid sequence has been completed;
(iii) treating the dried resin nine times for 10 minutes each with a solution of 1% (v/v) trifluoroacetic acid (TFA) in dichloromethane (DCM) in order to deprotect the lysine side chain at position 14;
(iv) neutralizing the resin with a solution of 3% diisopropyl ethylamine (DIPEA) in DCM, until the pH of the solution remains at ≥8;
(v) coupling an activated Fmoc-Glu-OtBu linker moiety to the deprotected lysine side chain under basic conditions;
(vi) cleaving the Fmoc group of the linker coupled to the lysine side chain in step (v) with 20% (v/v) piperidine in DMF;
(vii) coupling activated palmitic acid to the deprotected terminal functional group of the linker of step (vi);
(viii) drying the resin;
(viii-a) analyzing the deprotection yield of step (iii) by cleaving a test sample of the resin bound peptide;
(viii-b) repeating steps (iii) to (viii-a) until the content of cleaved peptide containing the modified lysine side chain is at least 85%;
(ix) cleaving the peptide from the resin using a cleavage cocktail consisting of 96.0-97.5% (w/w) TFA, 1,7-2.6% (w/w) EDT and 0.7-1.5% (w/w) 3-methylindole;
(x) filtering the peptide solution after cleavage at room temperature;
(xi) distilling the filtered peptide solution under vacuum at ≤30° C.;
(xii) adding the residual fraction from the distillation to an antisolvent consisting of DIPE and n-heptane in a ration of from 25:75 (v/v) to 35:65 (v/v);
(xiii) stirring the precipitated solution at 10-15° C. for 1-18 hours;
(xiv) filtering the precipitated solution;
(xv) washing the precipitate 4-5 times by (xv-a) resuspending the precipitate in ethyl acetate, (xv-b) stirring the resulting suspension for 30-60 minutes and (xv-c) filtering off ethyl acetate; and
(xvi) drying the wet peptide under vacuum.

20. The method of claim 1, wherein, in step (iii), the dried resin is treated at least nine times for at least 10 minutes, with a solution of about 1% (v/v) TFA in DCM.

21. The method of claim 1, wherein, in step (iii), the dried resin is treated at least nine times for at least 15 min, with a solution of about 1% (v/v) TFA in DCM.

22. The method of claim 17, wherein in step (xii), the antisolvent is a mixture consisting of diisopropyl ether (DIPE) and n-heptane in a ratio of from 25:75 (v/v) to 35:65 (v/v).

23. The method of claim 1, wherein the exendin-4 derivative has a length of between 30 and 44 amino acids, and wherein the sequence identity to wild-type exendin-4 in the region corresponding to amino acids 1-13 of wild-type exendin is at least 65%.

24. A method of preparing an isolated exendin-4 derivative peptide comprising a lipophilically modified lysine side chain, comprising the steps of:
(i) assembling the amino acid sequence of said peptide with protected reactive functional groups in the side chains in a step-wise manner using solid phase peptide synthesis (SPPS), wherein the side chain of lysine to be modified is protected by a trityl-based protecting group;
(ii) drying the solid phase resin after the assembling of the amino acid sequence has been completed;
(iii) treating the dried resin several times with a solution of 0.5 to 1.5% (v/v) trifluoroacetic acid (TFA) in dichloromethane (DCM) in order to deprotect the lysine side chain to be modified, wherein the number of TFA in DCM treatments is adjusted such that the yield of modified lysine side chain in step (ix) is at least 85% as compared to peptide without modified lysine side chain;
(iv) neutralizing the resin;
(v) coupling at least one activated 9-fluorenylmethyloxycarbonyl (Fmoc)-bound linker moiety to the deprotected lysine side chain;
(vi) deprotecting the terminal functional group of the linker coupled to the lysine side chain in step (v);
(vii) coupling an activated lipophilic moiety to the deprotected terminal functional group of the linker of step (vi);
(viii) drying the resin; and
(ix) cleaving the peptide from the resin,
thereby preparing the isolated exendin-4 derivative peptide comprising a lipophilically modified lysine side chain, wherein the exendin-4 derivative has a length of between 30 and 44 amino acids, and wherein the sequence identity to wild-type exendin-4 in the region corresponding to amino acids 1-13 of wild-type exendin is at least 65%.

* * * * *

SEQUENCE LISTING

```
<160> NUMBER OF SEQ ID NOS: 6

<210> SEQ ID NO 1
<211> LENGTH: 39
<212> TYPE: PRT
<213> ORGANISM: Artificial Sequence
<220> FEATURE:
<223> OTHER INFORMATION: Exendin-4 analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 1

His Xaa Gln Gly Thr Phe Thr Ser Asp Leu Ser Lys Gln Lys Glu Ser
1               5                   10                  15

Lys Ala Ala Gln Asp Phe Ile Glu Trp Leu Lys Ala Gly Gly Pro Ser
            20                  25                  30

Ser Gly Ala Pro Pro Ser
        35

<210> SEQ ID NO 2
<211> LENGTH: 39
<212> TYPE: PRT
<213> ORGANISM: Artificial Sequence
<220> FEATURE:
<223> OTHER INFORMATION: Exendin-4 analogue (side product)
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (39)..(39)
<223> OTHER INFORMATION: Ser is modified with an NH2-group
```

```
<400> SEQUENCE: 2

His Xaa Gln Gly Thr Phe Thr Ser Asp Leu Ser Lys Gln Lys Glu Ser
1               5                   10                  15

Lys Ala Ala Gln Asp Phe Ile Glu Trp Leu Lys Ala Gly Gly Pro Ser
            20                  25                  30

Ser Gly Ala Pro Pro Pro Ser
            35

<210> SEQ ID NO 3
<211> LENGTH: 39
<212> TYPE: PRT
<213> ORGANISM: Heloderma suspectum
<220> FEATURE:
<221> NAME/KEY: MOD_RES
<222> LOCATION: (39)..(39)
<223> OTHER INFORMATION: Ser is modified with an NH2 group

<400> SEQUENCE: 3

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
            35

<210> SEQ ID NO 4
<211> LENGTH: 30
<212> TYPE: PRT
<213> ORGANISM: Homo sapiens
<220> FEATURE:
<221> NAME/KEY: MOD_RES
<222> LOCATION: (30)..(30)
<223> OTHER INFORMATION: Arg is modified with an NH2 group

<400> SEQUENCE: 4

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 5
<211> LENGTH: 29
<212> TYPE: PRT
<213> ORGANISM: Homo sapiens

<400> SEQUENCE: 5

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 6
<211> LENGTH: 31
<212> TYPE: PRT
<213> ORGANISM: Artificial Sequence
<220> FEATURE:
<223> OTHER INFORMATION: Liraglutide
<220> FEATURE:
<221> NAME/KEY: MOD_RES
<222> LOCATION: (20)..(20)
<223> OTHER INFORMATION: Lys is functionalized at the amino side chain
      group as Lys((S)-4-carboxy-4-hexadecanoylamino-butyryl)

<400> SEQUENCE: 6
```

-continued

```
His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20              25                  30
```